(12) United States Patent
Samuelsson et al.

(10) Patent No.: US 11,672,792 B2
(45) Date of Patent: Jun. 13, 2023

(54) TOPICAL FORMULATIONS COMPRISING MONTELUKAST AND COMBINATIONS WITH MUSSEL ADHESIVE PROTEINS

(71) Applicant: ENLITISA (SHANGHAI) PHARMACEUTICAL CO., LTD, Shanghai (CN)

(72) Inventors: Bengt Ingemar Samuelsson, Stockholm (SE); Ming Gu, Jiangyin (CN)

(73) Assignee: ENLITISA (SHANGHAI) PHARMACEUTICAL CO., LTD, Shanghai (CN)

( * ) Notice: Subject to any disclaimer, the term of this patent is extended or adjusted under 35 U.S.C. 154(b) by 0 days.

(21) Appl. No.: 16/628,170

(22) PCT Filed: Jul. 4, 2018

(86) PCT No.: PCT/CN2018/094441
§ 371 (c)(1),
(2) Date: Jan. 2, 2020

(87) PCT Pub. No.: WO2019/007356
PCT Pub. Date: Jan. 10, 2019

(65) Prior Publication Data
US 2021/0145819 A1 May 20, 2021

(30) Foreign Application Priority Data

Jul. 5, 2017 (WO) ............... PCT/CN2017/091819
May 16, 2018 (WO) ............... PCT/CN2018/087058

(51) Int. Cl.
| | |
|---|---|
| A61K 38/00 | (2006.01) |
| A61K 31/47 | (2006.01) |
| A61P 17/02 | (2006.01) |
| A61P 17/04 | (2006.01) |
| A61K 9/00 | (2006.01) |
| A61K 9/06 | (2006.01) |
| A61K 38/08 | (2019.01) |
| A61K 38/17 | (2006.01) |
| A61K 47/10 | (2017.01) |

(52) U.S. Cl.
CPC ............ *A61K 31/47* (2013.01); *A61K 9/0014* (2013.01); *A61K 9/0075* (2013.01); *A61K 9/06* (2013.01); *A61K 38/08* (2013.01); *A61K 38/1767* (2013.01); *A61K 47/10* (2013.01); *A61P 17/02* (2018.01); *A61P 17/04* (2018.01)

(58) Field of Classification Search
CPC .... A61K 31/47; A61K 9/0014; A61K 9/0075; A61K 9/06; A61K 38/08; A61K 38/1767; A61K 47/10; A61P 17/02; A61P 17/04
See application file for complete search history.

(56) References Cited

U.S. PATENT DOCUMENTS

| | | | |
|---|---|---|---|
| 6,987,170 B1 * | 1/2006 | Silverman ............ | C07K 5/1013 |
| | | | 435/69.1 |
| 9,044,479 B2 | 6/2015 | May | |
| 10,548,837 B1 | 2/2020 | Avramoff et al. | |
| 2003/0207932 A1 | 11/2003 | Mann | |
| 2011/0124681 A1 | 5/2011 | Schlesinger | |
| 2012/0165299 A1 | 6/2012 | Sharma | |
| 2022/0105082 A1 * | 4/2022 | Samuelsson ............... | A61P 1/10 |

FOREIGN PATENT DOCUMENTS

| | | | | |
|---|---|---|---|---|
| CN | 1961867 A | 5/2007 | | |
| CN | 101773503 A | 7/2010 | | |
| CN | 102596194 A | 7/2012 | | |
| CN | 103002896 A | 3/2013 | | |
| CN | 103239450 B | 8/2013 | | |
| CN | 103655497 A | 3/2014 | | |
| CN | 104168892 B | 11/2014 | | |
| CN | 104784157 B | 7/2015 | | |
| CN | 105769825 A | 7/2016 | | |
| CN | 105878215 A | 8/2016 | | |
| IN | 201301762 | 6/2013 | | |
| WO | 2007126865 A2 | 11/2007 | | |
| WO | WO-2007126865 A2 * | 11/2007 | ........... | A61K 9/0048 |
| WO | 2008/105803 A1 | 9/2008 | | |
| WO | 2008/106081 A1 | 9/2008 | | |
| WO | WO-2008106081 A1 * | 9/2008 | ............ | A61K 31/38 |
| WO | 2011027119 A | 3/2011 | | |

(Continued)

OTHER PUBLICATIONS

Turtay et al. Effects of montelukast on burn wound healing in rat model. Clinical & Investigative Medicine 2010. (Year: 2010).*
Zhou et al. Montelukast attenuates neuropathic pain through inhibiting p38 mitogen-activated protein kinase and nuclear factor-kappa B in a rat model of chronic constriction injury. Anesth Analg. May 2014; 118(5):1090-6). (Year: 2014).*
Haisar et al. Effects of Montelukast in an Acute Experimental Rectocolitis Model in Sprague Dawley Rats. American Journal of Gastroenterology: Oct. 2009—vol. 104—Issue—p. S446. (Year: 2009).*
Attwood et al. Eosinophilic oesophagitis: a novel treatment using Montelukast. Gut 2003;52:181-185. (Year: 2003).*

(Continued)

*Primary Examiner* — Aradhana Sasan
*Assistant Examiner* — Mercy H Sabila
(74) *Attorney, Agent, or Firm* — Troutman Pepper Hamilton Sanders LLP (Rochester)

(57) ABSTRACT

There is provided topical pharmaceutical formulations comprising montelukast, or a pharmaceutical acceptable salt of solvate thereof, as well as combination products comprising (a) at least one mussel adhesive protein or a derivative thereof; and (b) montelukast, or a pharmaceutically-acceptable salt or solvate thereof. The formulations and combination products find particular utility in direct topical administration for the treatment of inflammation, of inflammatory disorders and/or of condition characterized by inflammation, including wounds, burns, psoriasis, acne and atopic dermatitis.

19 Claims, 12 Drawing Sheets
Specification includes a Sequence Listing.

(56) References Cited

FOREIGN PATENT DOCUMENTS

| WO | 2011159821 A | 12/2011 | | |
|---|---|---|---|---|
| WO | WO-2014164282 A1 | * | 10/2014 | ............... A61P 25/00 |
| WO | WO-2016148455 A2 | * | 9/2016 | ............... A61K 47/28 |
| WO | 2017011982 | | 1/2017 | |
| WO | WO-2017011983 A1 | * | 1/2017 | ............... A61K 9/06 |

OTHER PUBLICATIONS

Muraki et al. Inhaled montelukast inhibits cysteinyl-leukotriene-induced bronchoconstriction in ovalbumin-sensitized guinea-pigs: the potential as a new asthma medication. International Immunopharmacology 9 (2009) 1337-1341)... (Year: 2009).*
Basyigit et al. Anti-inflammatory effects of montelukast on smoke-induced lung injury in rats Multidiscip. Respir. Med. 2010; 5(2): 92-98. (Year: 2010).*
Sener et al. Leukotriene receptor blocker montelukast protects against burn-induced oxidative injury of the skin and remote organs. Burns 31 (2005) 587-596 (Year: 2005).*
International Search Report and Written Opinion for corresponding Application No. PCT/CN2017/091819 (dated Apr. 16, 2018).
Beller et al, "Cysteinyl Leukotriene 1 Receptor Controls the Severity of Chronic Inflammation and Fibrosis", PNAS 101 (9): 3047-3052 (2004).
El-Hossary et al, "Montelukast as a New Topical Ocular Therapeutic Agent for Treatment of Allergic Conjunctivitis: An Experimental Comparative Study", Aust. J. Basic & Appl. Sci. 4(1):71-78 (2010).
Ehayel et al, "Montelukast Treatment in Children with Moderately Severe Atopic Dermatitis", Eur. Ann. Allergy. Clin. Immunol. 39(7): 232-236 (2007).
Friedmann et al, "A Double-Blind, Placebo-Controlled trial of Montelukast in Adult Atopic Eczema", Clin. Exp. Allergy 37:1536-1540 (2007).
Femiano et al, "Pilot Study on Recurrent Aphthous Stomatitis (RAS): A Randomized Placebo-Controlled Trial for the Comparative Therapeutic Effects of Systemic Prednisone and Systemic Montelukast in Subjects Unresponsive to Topical Therapy", Oral Surg. Oral Med. Oral Path. Oral Radiol. Endod. 109(3):402-407 (2010).
Gao et al, "Review on Mussel Adhesive Protein", Journal of Anhui Agr. Sci. 39(32):19860-19862 (2011).
Hon et al, "Clinical Effectiveness and Safety of Montelukast in Asthma. What are the Conclusions from Clinical Trials and Meta-Analyses?", Drug Design, Development and Therapy 8:839-850 (2014).
Jullaphant et al, "Montelukast Nasal Spray: Formulation Development and in vitro Evaluation", Pharm. Dev. Technol. 24(4):494-503 (2019).
Kabasakal et al, "Burn-Induced Oxidative Injury of the Gut is Ameliorated by the Leukotriene Receptor Blocker Montelukast", Prostaglandins Leukot. Essent. Fatty Acids 72:431-440 (2005).
Leonardi et al., Leukotriene Antagonist Drugs as Treatment of Allergic Conjunctivitis and Comorbidities in Children, Conjunctivitis—A Complex and Multifaceted Disorder, Zdenek Pelikan, IntechOpen 7:111-126 (2011).
Papathanassiou et al, "Leukotriene Antagonists Attenuate Late Phase Nitric Oxide Production During the Hypersensitivity Response in the Conjunctiva", Inflamm. Res. 53:373-376 (2004).
Shimbori et al, "Pranlukast, a Cysteinyl Leukotriene Type 1 Receptor Antagonist, Attenuates the Progression but not the Onset of Silica-Induced Pulmonary Fibrosis in Mice", Int. Arch. Allergy Immunol. 158:241-251 (2012).
Sardana et al, "A Comparison of Intranasal Corticosteroid, Leukotriene Receptor Antagonist, and Topical Antihistamine in Reducing Symptoms of Perennial Allergic Rhinitis as Assessed Through the Rhinitis Severity Score", Allergy Asthma Proc. 31(1):5-9 (2010).
Sener et al., "Leukotriene Receptor Blocker Montelukast Protects Against Burn-Induced Oxidative Injury of the Skin and Remote Organs", Burns 31:587-596 (2005).
Struck et al, "Zum Einfluβ Nichtsteroidaler Antiphlogistika Auf Die EntzUndungsreaktion", Opthalmologe 92:849-853 (1995) (English abstract only, autotranslated).
Theron et al,."Cysteinyl Leukotriene Receptor-1 Antagonists as Modulators of Innate Immune Cell Function", J. Immunol. Res., Article ID 608930, 16 pp. (2014).
Tatar et al, "The Effect of Combined Medical Treatment on Quality of Life in Persistent Allergic Rhinitis", Indian J. Otolaryngol. Head Neck Surg. 65(Suppl 2):S333-S337 (2013).
Turtay et al, "Effects of Montelukast on Burn Wound Healing in a Rat Model", Clin. Invest. Med. 33(6):E413-E421 (2010).
Vinuesa et al, "Montelukast Trealment (Cysteinyl Leukotriene Receptor Antagonist) in a Model of Food Allergy Modifications in Lymphatic Cell Population from Rectal Mucosa", Rev. Esp. Enferm. Dig. 102(7):421-425 (2010).
Yanase et al, "The Leukotriene Antagonist Montelukast as a Therapeutic Agent for Atopic Dermatitis", J. Am. Acad. Dermatol. 44(1):89-93 (2001).
Yokomizo et al, "Leukotriene Receptors as Potential Therapeutic Targets", J. Clin. Invest. 128(7):2691-2701 (2018).
Zhao et al, "Montelukast, a Cysteinyl Leukotriene Receptor-1 Antagonist, Attenuates Chronic Brain Injury after Focal Cerebral Ischaemia in Mice and Rats", J. Pharm. Pharmacol., 63:550-557 (2011).
Zhu et al, "Composition, Working Mechanism and Application of Mussel Adhesive Protein", Translation Advances in Marine Science 32(4):560-570 (2014).
International Search Report and Written Opinion for corresponding Application No. PCT/CN2018/094441 (dated Sep. 27, 2018).
Holma et al., "Prophylactic Potential Of Montelukast Against Mild Colitis Induced by Dextran Sulphate Sodium in Rats," J. Physiol. Pharmacol. 58(3):455-467 (2007).
Ersoy et al., "Leukotriene D4 Receptor Antagonist Montelukast Alleviates Water Avoidance Stress-Induced Degeneration of the Gastrointestinal Mucosa," Prostaglandins Leukot. Essent. Fatty Acids 78(3):189-197 (2008).
Tolazzi et al., "Influence of Leukotriene Inhibitor Montelukast on Wound Contraction and Cutaneous Healing Process in Rats," Aesthetic Plast. Surg. 33(1):84-89 (2009).
Shepherd, "The Role of The Surgical Technologist in Wound Management," The Surgical Technologist 255-261 (Jun. 2009).
Sun and Migaly, "Review of Hemorrhoid Disease: Presentation Management," Clin. Colon Rectal Surg., 29:22-29 (2016).
Naito, M., "Functional Materials That Mimic Marine Fouling Organisms," J. Jpn. Soc. Colour Mater. 87(1):13-18 (2014).

* cited by examiner

Control group

Test group

Right Side (a)  (b)  (c)

Left Side (a)  (b)  (c)

(a)

(b)

100 US 11,672,792 B2

```
                        SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: MAP peptide
<220> FEATURE:
<221> NAME/KEY: SITE
<222> LOCATION: 6,7
<223> OTHER INFORMATION: Wherein Xaa is hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 1

Ala Lys Pro Ser Tyr Xaa Xaa Thr Xaa Lys
1               5                   10
```

TOPICAL FORMULATIONS COMPRISING MONTELUKAST AND COMBINATIONS WITH MUSSEL ADHESIVE PROTEINS

This application is a national stage application under 35 U.S.C. § 371 of PCT Application No. PCT/CN2018/094441, filed Jul. 4, 2018, which claims the priority benefit of PCT Application No. PCT/CN2018/087058, filed May 16, 2018, and PCT Application No. PCT/CN2017/091819, filed Jul. 5, 2017.

FIELD OF THE INVENTION

This invention relates to novel pharmaceutical combinations and to novel pharmaceutical uses and compositions.

Background and Prior Art

Inflammation is typically characterised as a localised tissue response to e.g. invasion of microorganisms, certain antigens, damaged cells or physical and/or chemical factors. The inflammatory response is normally a protective mechanism which serves to destroy, dilute or sequester both the injurious agent and the injured tissue, as well as to initiate tissue healing.

Inflammation may result from physical trauma, infection, some chronic diseases (e.g. psoriasis and autoimmune diseases, such as rheumatoid arthritis) and/or chemical and/or physiological reactions to external stimuli (e.g. as part of an allergic response). A complex series of events may be involved, in which inflammatory mediators increase blood flow and dilation of local blood vessels, resulting in redness and heat, the exudation of fluids, often resulting in localised swelling, leukocytic migration into the inflamed area, and pain.

Many conditions/disorders are characterized by, and/or are caused by, abnormal, tissue-damaging inflammation. Such conditions are typically characterized by activation of immune defence mechanisms, resulting in an effect that is more harmful than beneficial to the host, and are generally associated with varying degrees of tissue redness or hyperemia, swelling, hyperthermia, pain, itching, cell death, tissue destruction, cell proliferation and/or loss of function. Examples include inflammatory bowel diseases, rheumatoid arthritis, multiple sclerosis, psoriasis, glomerulonephritis and transplant rejection.

Typically, a complex series of events results in inflammatory changes such as increased blood flow through dilation of local blood vessels, resulting in redness and heat, the extravasation of leukocytes and plasma, often resulting in localised swelling, activation of sensory nerves (resulting in pain in some tissues) and loss of function. These inflammatory changes are triggered by a cascade of cellular and biochemical events involving cells like neutrophils, monocytes, macrophages and lymphocytes together with inflammatory mediators such as vasoactive amines, cytokines, complement factors and reactive oxygen species.

Amongst other things, inflammation plays a key role in the wound healing process. Wounds and burns can therefore be classified as conditions with which inflammation is associated. Traditional thinking in the art is that antiinflammatory drugs should not be applied directly to open wounds, as this would be detrimental to the progress of wound healing.

Mussel adhesive protein (MAP), also known as *Mytilus edulis* foot protein (mefp), is a protein secreted by marine shellfish species, such as *Mytilus edulis, Mytilus coruscus* and *Perna viridis*. The adhesive protein is secreted by mussels from the byssus gland where it is produced and stored. When secreted on a surface of a solid, such as a rock, but also other solid objects, such as metals, wood, glass, etc., a water-proof bond is formed which fixes the mussel to the solid object. Mussels are typically attached, in groups, to coastal reefs or to the bottoms of ships. The bond is incredibly strong, having the ability to resist wave impacts in coastal waters.

Studies on *Mytilus edulis, Mytilus galloprovincialis, Mytilus californias* and *Perna viridis* have thus far identified eleven separate adhesive protein subtypes derived from mussels: mfp-1 (sometimes referred to as "mefp-1", hereinafter used interchangeably), mfp-2/mefp-2, mfp-3/mefp-3, mfp-4/mefp-4, mfp-5/mefp-5, mfp-6/mefp-6; the collagens pre-COL-P, pre-COL-D and pre-COL-NG; and the mussel feet matrix proteins PTMP (proximal thread matrix protein) and DTMP (distal proximal thread matrix protein). See, for example, Zhu et al, *Advances in Marine Science*, 32, 560 (2014) and Gao et al, *Journal of Anhui Agr. Sci.*, 39, 19860 (2011)).

All mussel adhesive proteins, including sub-types thereof, have two structural characteristics, in that they comprise: (1) lysine, such that the protein carries a high positive charge loading (due to the $NH_2$ termini); (2) 3,4-dihydroxyphenylalanine (DOPA, dopamine), the catechol part of which is responsible for the formation of strong covalent bonds and consequently the ability of mussel adhesive proteins to bind to solid surfaces.

Products based on mussel adhesive protein products are presently used in a limited number of fields (including micro-cellular bonding, as tissue bonding agents and the treatment of wounds and burns). Commercial products are either directly used as a solution of mussel adhesive protein or are stored as a freeze-dried powder for dissolution prior to use.

Montelukast is an orally-active non-steroidal immunomodulating compound that is administered perorally to the gastrointestinal tract for the maintenance treatment and prevention of symptoms of seasonal allergies (see e.g. Hon et al, Drug Design, Development and Therapy, 8, 839 (2014)). It acts by blocking the action of, primarily, leukotriene D4 (as well as leukotrienes C4 and E4) on the cysteinal leukotriene receptor CysLT1 in the airways.

Although its potential use in the treatment of various other inflammatory disorders has been described in the literature, to the applicant's knowledge, montelukast has never been administered topically, for example to the skin, to treat inflammation.

Furthermore, to the applicant's knowledge, the use of combination products comprising, specifically, a mussel adhesive protein and montelukast to treat, for example, inflammation, is not specifically disclosed in the prior art.

DISCLOSURE OF THE INVENTION

According to a first aspect of the invention, there is provided a combination product comprising:

(a) at least one mussel adhesive protein or a derivative, such as a pharmaceutically-acceptable derivative, thereof; and (b) montelukast, or a pharmaceutically-acceptable salt or solvate thereof, which combination products are referred to hereinafter as "the combination products according to the invention".

In the context of the present invention, the term "a mussel adhesive protein" includes any adhesive protein that may be derived from mussel species, including those mentioned herein and preferably *Mytilus edulis* (blue mussel).

The term thus include full length proteins, including all sub-types, that are or may be derived from mussels, such as the collagens pre-COL-P, pre-COL-D and pre-COL-NG, the mussel feet matrix proteins PTMP and DTMP, and, more preferably, mfps or mefps, such as mefp-2, mefp-3, mefp-4, mefp-5, mefp-6 and especially mefp-1, and includes mixtures or combinations of any of these proteins, such as mefps. Although mixtures/combinations of the aforementioned MAP sub-types may be provided as the MAP "component" in accordance with the invention, we prefer that the purity of the principal MAP sub-type (e.g. mefp-1) is at least 25% by weight of the total amount of any such mixture.

The at least one mussel adhesive protein that is an essential element of the combination products of the invention is hereinafter referred to the at least one "MAP". Mussel adhesive proteins are referred to together hereinafter, collectively or separately, as "MAPs".

Known methods of extracting, preparing, separating and purifying naturally-occurring MAPs may be employed, for example mixed adsorption chromatography (see Chinese Patent No. ZL200710179491.0), carboxymethyl ion exchange chromatography (see Chinese Patent No. ZL200710179492.5), and/or salting out and dialysis (Chinese Patent No. ZL200910087567.6). Commercial sources of MAPs include USUN Bio Co. (China; sold as MAP Medical Device®), BD Biosciences (USA), Kollodis (South Korea) and Biopolymer (Sweden). MAPs may alternatively be produced using known recombinant DNA methods.

Derivatives of MAPs Include isolated pharmaceutically-acceptable derivatives, such as lower molecular weight products (for example with a molecular weight in the range of about 500 Da to about 2,000 (e.g. about 1,200, such as about 800) Da, which may allow for easier permeation through biological membranes, such as the skin barrier or a mucosal surface. Such derivatives may also include other compounds that comprise amino acid sequences that are the same as, or are (e.g. minor) variants of, sequences that have been identified in naturally-occurring MAPs, and which may be synthesized by chemical and/or biological processes (e.g. chemical modifications of naturally-occurring MAPs, or direct synthesis). By "(e.g. minor) variants of amino acid sequences identified in naturally-occurring MAPs", we mean variations in those sequences that do not negatively affect the requisite properties of the relevant naturally-occurring MAP to a measurable degree.

Derivatives of MAPs include "MAP Peptide" and salts (e.g. cationic salts) thereof, which is a decapeptide of the sequence: Ala-Lys-Pro-Ser-Tyr-Hyp-Hyp-Thr-DOPA-Lys (SEQ ID NO: 1) (see Waite, *Int. J. Adhesion and Adhesives*, 7, 9 (1987)). MAP Peptide may derived and/or isolated as a low molecular weight derivative of naturally-occurring MAPs, or may be synthesized, for example as described by Yamamoto in *J. Chem. Soc., Perkin Trans.* 1, 613 (1987). See also Dalsin et al, *J. Am. Chem. Soc.*, 125, 4253 (2003).

Such derivatives of MAPs may be employed in combination products according to the invention alone, or in combination with one or more other such derivatives, and/or one or more of the aforementioned full length MAPs.

Pharmaceutically-acceptable salts of montelukast that may be mentioned include acid addition salts and base addition salts. Such salts may be formed by conventional means, for example by reaction of active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Preferred salts include, for example, hydrochloride, bisulfate, maleate, mesylate, tosylate, alkaline earth metal salts, such as calcium and magnesium, or alkali metal salts, such as sodium and potassium salts. Preferred salts of montelukast include sodium salts and dicyclohexylamine salts.

Montelukast may be employed in enantiomerically-enriched form. By "enantiomerically-enriched" we mean, respectively, any mixture of the enantiomers of montelukast, in which one isomer is present in a greater proportion than the other. For example, enantiomers of montelukast with optical purities (enantiomeric excess; e.e.) of greater than 90% may be employed.

Combination products according to the invention provide for the administration of at least one MAP or a (e.g. pharmaceutically-acceptable) derivative thereof in conjunction with montelukast or a pharmaceutically-acceptable salt or solvate thereof, and may thus be presented either as separate formulations, wherein at least one of those formulations comprises a MAP/derivative, and at least one comprises montelukast/salt/solvate, or may be presented (i.e. formulated) as a combined preparation (i.e. presented as a single formulation including MAP/derivative and montelukast/salt/solvate).

Thus, there is further provided:

(1) a pharmaceutical formulation including at least one MAP or derivative thereof; montelukast, or a pharmaceutically-acceptable salt or solvate thereof; and a pharmaceutically-acceptable adjuvant, diluent or carrier (which formulation is hereinafter referred to as a "combined preparation"); and (2) a kit of parts comprising components:

(A) a pharmaceutical formulation including at least one MAP or derivative thereof, in admixture with a pharmaceutically-acceptable adjuvant, diluent or carrier; and (B) a pharmaceutical formulation including montelukast, or a pharmaceutically-acceptable salt or solvate thereof, in admixture with a pharmaceutically-acceptable adjuvant, diluent or carrier, which components (A) and (B) are each provided in a form that is suitable for administration in conjunction with the other.

According to a further aspect of the invention, there is provided a method of making a kit of parts as defined above, which method comprises bringing component (A), as defined above, into association with a component (B), as defined above, thus rendering the two components suitable for administration in conjunction with each other.

By bringing the two components "Into association with" each other, we include that components (A) and (B) of the kit of parts may be:

(i) provided as separate formulations (i.e. Independently of one another), which are subsequently brought together for use in conjunction with each other in combination therapy; or (ii) packaged and presented together as separate components of a "combination pack" for use in conjunction with each other in combination therapy.

Thus, there is further provided a kit of parts comprising:

(I) one of components (A) and (B) as defined herein; together with (II) instructions to use that component in conjunction with the other of the two components.

The kits of parts described herein may comprise more than one formulation including an appropriate quantity/dose of a MAP/derivative, and/or more than one formulation including an appropriate quantity/dose of montelukast/salt/solvate, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by "administration in conjunction with", we include that respective formulations comprising a MAP (or derivative thereof) and montelukast (or salt/solvate thereof) are administered, sequentially, separately and/or simultaneously, over the course of treatment of the relevant condition.

Thus, in respect of the combination product according to the invention, the term "administration in conjunction with" includes that the two components of the combination product (MAP and montelukast) are administered (optionally repeatedly), either together, or sufficiently closely in time, to enable a beneficial effect for the patient, that is greater, over the course of the treatment of the relevant condition, than if either a formulation comprising MAP, or a formulation comprising montelukast, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to the invention, the term "in conjunction with" includes that one or other of the two formulations may be administered (optionally repeatedly) prior to, after, and/or at the same time as, administration of the other component. When used in this context, the terms "administered simultaneously" and "administered at the same time as" include that individual doses of the relevant MAP and montelukast are administered within 48 hours (e.g. 24 hours) of each other.

The combination products according to the invention find utility in the treatment of inflammation. The "treatment of inflammation" includes the treatment of inflammation in any organ of the body (including soft tissue, joints, nerves, the vascular system, Internal organs, especially mucosal surfaces, and particularly the skin), irrespective of the cause, and also includes all such inflammatory disorders or conditions, and/or disorders or conditions characterized by inflammation (e.g. as a symptom).

Inflammatory conditions may be (and are typically) characterized by activation of immune defence mechanisms, resulting in an effect that is more harmful than beneficial to the host. Such conditions are generally associated with varying degrees of tissue redness or hyperemia, swelling, hyperthermia, pain (including aching), exudation of body fluids, itching (pruritis), cell death and tissue destruction, cell proliferation, and/or loss of function.

Inflammatory conditions that may be mentioned include arteritis, diabetes mellitus, metabolic syndrome, rosacea, asthma and allergy, ankylosing spondylitis, chronic obstructive pulmonary disease, gouty arthritis, inflammatory bowel disease (such as Crohn's disease and ulcerative colitis), multiple sclerosis, osteoarthritis, pancreatitis, prostatitis, psoriatic arthritis, rheumatoid arthritis, tendinitis, bursitis, Sjogren's syndrome, systemic lupus erythematosus, uveitis, urticaria, vasculltis, mastocytosis, diabetic vascular complications, migraine, atherosclerosis and associated cardiovascular disorders. A disease state that may be specifically mentioned is chronic obstructive pulmonary disease (COPD).

Inflammatory conditions that may be more especially mentioned include inflammations of the skin or mucosa (including the oral, nasal, ocular, vaginal, cervical and/or anorectal mucosae, more particularly the oral or nasal mucosae), such as inflammation resulting from infections (such as viral and/or bacterial infections), or allergic/atopic conditions (such as rhinitis, pharyngitis, periodontitis, gingivitis, xerophthalmia, conjunctivitis, dermatitis, urticaria (hives) and food allergy); and other inflammatory conditions, such as herpes, drug eruptions, polymorphous light eruptions, sunburn, early manifestations of skin cancers (erythema-like skin lesions), pathological hair loss (including following skin grafting), chemo rash, psoriasis, erythema multiforme, folliculitis, eczema and external otitis.

More particularly, combination products according to the invention may be used to treat certain conditions characterized by inflammation, and/or with which inflammation is associated. Such conditions may include wounds (including abrasions (scratches), incisions (including operative incisions), lacerations, punctures, avulsions, bruising and scarring), burns (including inflammation resulting from surgery following burns, such as skin grafting), and other conditions, such as hemorrhoids.

Wounds of the skin or mucosa may arise from internal or external physical injury to the membrane surface, or may be caused by (i.e. be a symptom of an underlying physiological disorder).

Physical (e.g. "open") wounds may be caused by sharp objects (cuts, incisions, punctures) or blunt objects/mechanical forces (lacerations, abrasions, avulsions), physical blows (bruises), heat or chemicals (burns and blisters), UV light (sunburn), cold (chilblains or frostbite). Wounds may be superficial (damage only to the epidermis and/or dermis) or may be full thickness wounds (damage below the epidermis and/or dermis). In serious cases, subcutaneous and/or submucosal tissues, such as muscles, bones, joints, and even internal organs, may be damaged.

The combination products of the invention may be used to treat not only the inflammation, pain (including aching) and/or pruritis (itching) associated with the wound itself and the healing process, but also they may be used to prevent the exudation of body fluids from wounds, the risk of infection, and also the prevention of physiological reactions that result from inflammation and/or wound healing processes, such as scarring and melanin pigmentation.

Scarring is a consequence of inflammation and/or wound healing and is a general term for the formation of fibrotic tissue that is a consequence of such inflammation/healing.

Combination products of the invention may also be useful in the suppression of the production of melanin pigmentation that may result from inflammation and/or wound healing. Combination products of the invention may also be useful in the suppression of disorders associated with melanin pigmentation, such as chloasma, freckles, melanosis, malar rash and other chromatosis, skin cancers with melanoma, and chromatosis that is caused by exposure to the sun or skin diseases like acne.

Wounds may also arise as a consequence of diseases or disorders. Such may include blistering and/or ulcers of the skin and mucosa. These are common conditions that are often long-lasting and difficult to treat. Skin tissues can often be damaged, removed, liquefied, infected and/or necrotic. Ulcers can lead to secondary consequences to health particularly if they become infected, are hard to heal and are costly. They can also cause significant psychological stress and economic loss to patients, affecting both general well-being and quality of life.

In the alternative, inflammatory skin conditions or diseases in which combination products according to the invention find particular utility include psoriasis, acne, eczema and dermatitis, especially allergic/atopic dermatitis.

Psoriasis is a chronic, inflammatory skin disease with a tendency to recur (some patients never heal during their entire life). Clinical manifestations of psoriasis mainly include erythema and scales. It can occur over the whole body, but is more commonly observed on the scalp and limbs.

Acne is a follicular (pilosebaceous unit) chronic, inflammatory skin disease, the occurrence of which is closely related to main factors like hypersteatosis, blocked pilosebaceous ducts (including closed and open comedones), bacterial infection and inflammatory reactions, that tends to occur during youth, characterised by multiform skin lesions on the face. The term acne thus includes regular acne and acne rosacea (i.e. copper nose).

Eczema is a skin inflammatory reaction with strong itching caused by a variety of internal and external factors. It has three phases, acute, sub-acute, and chronic. In the acute phase, there is a tendency for the production of exudates, while the chronic phase includes infiltration and hypertrophy. Skin lesions are often itchy and recur easily.

Dermatitis is a common skin disease characterised by coarseness, redness, itching, eczema, and dryness. Small lumps, refractory ulcers, and pigmented spots caused by dermatitis may, if not treated promptly, develop to basal cell carcinoma, squamous cell carcinoma, and malignant melanoma. Dermatitis may be caused by various internal and external infectious or non-infectious factors, including substances (contact dermatitis) or allergy (allergic/atopic dermatitis). Also included is seborrheic dermatitis (seborrheic eczema) and all forms of steroid-dependent dermatitis (including light-sensitive seborrheid, perioral dermatitis, rosacea-like dermatitis, steroid-rosacea, steroid-induced rosacea, iatrosacea, steroid dermatitis resembling rosacea, topical corticosteroid-induced rosacea-like dermatitis and, more particularly, facial corticosteroid addictive dermatitis (FCAD) or facial corticosteroid-dependent dermatitis (FCDD), as characterised by flushing, erythema, telangiectasia, atrophy, papules and/or pustules in the facial area after long-term treatment with (including uncontrolled use, abuse or misuse of) topical corticosteroids; see, for example, Xiao et al. *J. Dermatol.*, 42, 697 (2015) and Lu et al, *Clin. Exp. Dermatol.*, 35, 618 (2009)).

It has been found that combination products according to the invention may have positive effects in mitigating erythema, redness and swelling, edema, blisters, and bullous pemphigoid caused by various conditions including those mentioned generally and specifically herein, and may inhibit exudation of subcutaneous tissue fluid, and suppressing itching and pain caused by such inflammatory conditions.

Other inflammatory conditions that may be mentioned include:

(a) Mucosal Inflammation, such as oral mucositis, apthhous ulcers, otitis media, laryngitis, tracheitis, esophagitis, gastritis, enteritis and enterocolitis (including bacillary dysentery, chronic amoebic dysentery, schistosomiasis, nonspecific ulcerative colitis and regional enteritis), cervicitis and endocervicitis, endometritis, inflammation caused by inhalation injury and the like, as well as mucosal inflammation associated with cancers, and infections (e.g. viral infections, such as the common cold or influenza), that affect mucosal surfaces, such as those in the oral cavity, the nasopharynx, the ear, the throat, the trachea, the gastrointestinal tract, the cervix, etc.

(b) Orthopedic inflammation associated with, for example bone fractures, pyogenic infection of bones and joints, inflammation caused by rheumatic bone diseases, as well as pyogenic osteomyelitis (acute, chronic, localized, sclerotic, post-traumatic), pyogenic arthritis; bone tumors (osteoma, osteoid osteoma, chondroma), bone cysts, osteoclastoma, primary bone sarcoma (osteosarcoma, chondrosarcoma, osteofibrosarcoma, Ewing's sarcoma, non-Hodgkin's lymphoma, myeloma, chordoma), metastatic bone tumors, tumor-like lesions of bone (bone cyst, aneurysmal bone cyst, eosinophilic granuloma, fibrous dysplasla); and rheumatic arthritis.

(c) Nerve inflammation, such as peripheral polyneuritis, facial neuritis, peripheral neuritis, subcutaneous neuritis, ulnar neuritis, intercostal neuritis, etc.

(d) Subcutaneous and submucosal soft tissue inflammation, such as myositis, ligamentitis, tendonitis, panniculitis capsulitis, lymphadenitis, bubonadentitis, tonsillitis, synovitis, fasciitis, and soft tissue inflammation caused by injuries, contusion or laceration of muscles, ligaments, fascia, tendons, membrana synovialis, fat, articular capsules, and lymphoid tissue.

(e) Vascular inflammation, such as allergic leukocytoclastic vasculitis, allergic cutaneous vasculitis, polyarteritis nodosa, thrombotic vasculitis, granulomatous vasculitis, lymphocytic vasculltis, vasculitis with abnormalities in blood composition, and rheumatic vasculitis, as well as vascular inflammation associated with vascular cancers caused by allergic leukocytoclastic vasculitis, polyarteritis nodosa, thrombotic vasculitis, granulomatous vasculitis, lymphocytic vasculitis, vasculitis with abnormalities in blood composition, and rheumatic vasculitis.

(f) Inflammation of the internal organs, such as the heart, stomach, intestine, lung, liver, spleen, kidney, pancreas, bladder, ovary, and prostate, including but not limited to pericarditis, myocarditis, endocarditis, pneumonia, hepatitis, splenitis, nephritis pancreatitis, cystitis, oophoritis, prostatitis and treatment of gastric ulcer.

According to a further aspect of the invention there is provided a method of treatment of inflammation, of an inflammatory disorder, and/or of a disorder/condition characterized by inflammation (for example as a symptom), which method comprises the administration of a combination product according to the invention to a patient in need of such treatment.

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, inflammation and/or inflammatory disorders.

"Patients" Include reptilian and, preferably mammalian (particularly human) patients.

In accordance with the invention, MAPs/derivatives and montelukast/salt/solvate are preferably administered locally or systemically, for example orally, intravenously or intraarterially (including by intravascular and other perivascular devices/dosage forms (e.g. stents)), intramuscularly, cutaneously, subcutaneously, transmucosally (e.g. sublingually or buccally), rectally, Intravaginally, transdermally, nasally, pulmonarily (e.g. tracheally or bronchially), topically, or by any other parenteral route, in the form of a pharmaceutical preparation comprising the compound(s) In pharmaceutically acceptable dosage form(s). Administration by inhalation (e.g. nasally) is particularly useful when the condition to be treated is rhinitis or inflammation resulting from viral infections of the airways (common cold, Influenza). Pulmonary administration is particularly useful when the condition to be treated is COPD. Topical forms of administration may be enhanced by creating a spray comprising active ingredients, e.g. by using a powder aerosol or by way of an aqueous mist using an appropriate atomisation technique or apparatus, such as a nebulizer.

Preferred modes of delivery of MAPs and derivatives thereof include topically to the site of inflammation in an appropriate (e.g. pharmaceutically-acceptable) vehicle and/or a commercially-available formulation, but may also include oral, intravenous, cutaneous or subcutaneous, nasal, intramuscular, or intraperitoneal delivery. Modes of delivery of montelukast/salt/solvate that may be mentioned include oral delivery in known pharmaceutically-acceptable and/or commercially-available formulations, but may also include intravenous, cutaneous or subcutaneous, nasal, intramuscular, or intraperitoneal delivery, as well as administration topically to the site of inflammation in an appropriate (e.g. pharmaceutically-acceptable) vehicle.

MAP/derivative and montelukast will generally be administered together or separately in the form of one or more (e.g. pharmaceutical) formulations in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Such pharmaceutically acceptable carriers may also impart an immediate, or a modified, release of either active ingredient, whether administered together in a combined preparation or in the form of a kit of parts.

Suitable pharmaceutical formulations may be commercially available or otherwise prepared according to techniques that are described in the literature, for example, Remington *The Science and Practice of Pharmacy*, 22$^{nd}$ edition, Pharmaceutical Press (2012) and *Martindale*—The Complete Drug Reference, 38$^{th}$ Edition, Pharmaceutical Press (2014) and the documents referred to therein, the relevant disclosures in all of which documents are hereby incorporated by reference. Otherwise, the preparation of suitable formulations, and in particular combined preparations including both MAP/derivative and montelukast/salt/solvate may be achieved non-inventively by the skilled person using routine techniques.

Active ingredients (such as MAPs (for example Mefp-1) and derivatives thereof, and also montelukast) may be may be in the form of an aqueous formulation such as an emulsion, a suspension and/or a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution)), or a freeze-dried powder.

Active ingredients may in the alternative be combined with appropriate excipients to prepare:
  gel formulations (for which suitable gel matrix materials include cellulose derivatives, carbomer and alginates, gummi tragacanthae, gelatin, pectin, carrageenan, gellan gum, starch, Xanthan gum, cationic guar gum, agar, noncellulosic polysaccharides, vinyl polymers, acrylic resins, polyvinyl alcohol, carboxyvinyl polymer and, particularly, hyaluronic acid);
  lotions (condensates; for which suitable matrix materials include cellulose derivatives, glycerin, noncellulosic polysaccharides, polyethylene glycols of different molecular weights and propanediol);
  pastes or ointments (for which suitable paste matrix materials include glycerin, vaseline, paraffin, polyethylene glycols of different molecular weights, etc.);
  creams or foams (for which suitable excipients (e.g. foaming agents) include hydroxypropyl methyl cellulose, gelatin, polyethylene glycols of different molecular weights, sodium dodecyl sulfate, sodium fatty alcohol polyoxyethylene ether sulfonate, corn gluten powder and acrylamide);
  powder aerosols (for which suitable excipients include mannitol, glycine, dextrin, dextrose, sucrose, lactose, sorbitol and polysorbates); and/or
  liquid (aerosol) sprays for oral use or for inhalation (for which suitable excipients include viscosity modifiers, such as hyaluronic acid, emulsifiers, buffering agents, alcohols, water, preservatives, sweeteners, flavours, etc.).

Moisturizing agents, such as glycerol, glycerin, polyethylene glycol, trehalose, glycerol, petrolatum, paraffin oil, hyaluronic acid and salts (e.g sodium and potassium salts) thereof, octanoic/capyic triglyceride, and the like; and/or antioxidants, such as vitamins and glutathione; and/or pH modifiers, such as acids, bases and pH buffers, may also be included in such formulations, as appropriate. Furthermore, surfactants/emulsifiers, such as hexadecanol (cetyl alcohol), fatty acids (e.g. stearic acid), sodium dodecyl sulfate (sodium lauryl sulfate), sorbitan esters (e.g. sorbitan stearate, sorbitan oleate, etc.), monoacyl glycerides (such as glyceryl monostearate) polyethoxylated alcohols, polyvinyl alcohols, polyol esters, polyoxyethylene alkyl ethers (e.g. polyoxyethylene sorbitan monooleate), polyoxyethylene castor oil derivatives, ethoxylated fatty acid esters, polyoxylglycerides, lauryl dimethyl amine oxide, bile salts (e.g. sodium deoxycholate, sodium cholate), phospholipids, N,N-dimethyldodecylamine-N-oxide, hexadecyltrimethyl-ammonium bromide, poloxamers, lecithin, sterols (e.g. cholesterol), sugar esters, polysorbates, and the like; preservatives, such as phenoxyethanol, ethylhexy glycerin, and the like; and thickeners, such as acryloyldimethyltaurateNP copolymer may be included. In particular stearic acid, glyceryl monostearate, hexadecanol, sorbitan stearate, cetyl alcohol, octanoic/capric glyceride etc. may be included, particularly in cream formulations.

We have found that montelukast and salts thereof may be advantageously formulated for topical use as creams, lotions, waxes or, particularly, ointments, by formulating together with polyethylene glycols (PEGs) of different molecular weights, which can be any molecular weight between about 62 and about 22,000 (e.g. PEG 150, PEG, 200, PEG 350, PEG 400, PEG 600, PEG 800, PEG 1000, PEG 2000, PEG 3350, PEG 4000, PEG 6000). Montelukast may first be dissolved in a low molecular weight PEG, such as PEG 200 or, more particularly, PEG 400, to which other excipients, including PEGs of higher molecular weights (e.g. PEG 1000, PEG 3350, PEG 4000 or PEG 6000), solvents, such as lower alkyl alcohols (e.g. ethanol) or water, and/or other ingredients such as those listed above, may be added.

We have found unexpectedly that montelukast can be readily dissolved in such PEG-based solvents to make creams and ointments that have a lower pH (e.g. pH 5.9 to 7.5) rather than the higher pH (pH 9.5) that is observed in mainly aqueous formulations (e.g. water with a very low amount ethanol), and may irritate the skin or mucosal membranes. Montelukast can be solubilized in this way and then formulated into creams or ointments that are surprisingly stable (i.e. not prone to oxidation), with a pH that is more acceptable/less irritating to the skin/mucosa, and is closer to that of MAPs when they are dissolved in water.

Active ingredients (such as MAPs (for example Mefp-1) and derivatives thereof, and also montelukast), and (e.g. pharmaceutical) formulations (e.g. aqueous solutions, gels, creams, ointments, lotions/condensates, foams and/or pastes as described above) including them, may further be combined with an appropriate matrix material to prepare a dressing or a therapeutic patch for application on a biological surface, such as the skin or a mucosal surface. Such formulations may thus be employed to impregnate a matrix material, such as gauze, non-woven cloth or silk paper. The therapeutic patch may alternatively be, for example, a band-aid, a facial mask, an eye mask, a hand mask, a foot mask, etc.

Vaseline may be employed for use in applying such dressings to wounds, but we have also found that the PEG-based ointments described above may be combined with matrix materials to prepare dressings without the need to use vaseline.

Active ingredients (such as MAPs (for example Mefp-1) and derivatives thereof, and also montelukast) may also be combined in treatment with one or more growth factors selected from platelet-type growth factors (including platelet-derived growth factors, PDGFs); osteosarcoma-derived growth factors (ODGF), epidermal growth factors (EGFs), transforming growth factors (TGF$\alpha$ and TGF$\beta$), fibroblast growth factors ($\alpha$FGF, $\beta$FGF), insulin-like growth factors (IGF-I, IGF-II), nerve growth factors (NGF), interleukin-type growth factors (IL-1, IL-1, IL-3), erythropoietin (EPO), and colony stimulating factor (CSF).

Administration of active ingredients may be continuous or intermittent. The mode of administration may also be determined by the timing and frequency of administration, but is also dependent, in the case of the therapeutic treatment of inflammation, on the severity of the condition.

Depending on the disorder, and the patient, to be treated, as well as the route of administration, active ingredients may be administered at varying therapeutically effective doses to a patient in need thereof.

Similarly, the amount of active ingredients in a formulation will depend on the severity of the condition, and on the patient, to be treated, but may be determined by the skilled person.

Suitable doses of active ingredients include those referred to in the medical literature, such as *Martindale—The Complete Drug Reference*, 38$^{th}$ Edition, Pharmaceutical Press (2014) and the documents referred to therein, the relevant disclosures in all of which documents are hereby incorporated by reference.

In any event, the medical practitioner, or other skilled person, will be able to determine routinely the actual dosage, which will be most suitable for an individual patient, depending on the severity of the condition and route of administration. The above-mentioned dosages are exemplary of the average case; there can, of course, be individual instances where higher or lower dosage ranges are merited, and such are within the scope of this invention.

Peroral and topical doses may be administered between once and four times daily.

Appropriate concentrations of MAPs and derivatives thereof in an aqueous solution product may be about 0.01 (e.g. about 0.1) to about 15.0 (e.g. about 1.5) mg/mL, and appropriate pH values are in the range of about 1.0 to about 7.0 (for example about 3.0 to about 6.5), irrespective of whether the formulation employed is a combined preparation or a kit of parts as hereinbefore described. Suitable commercial sources of such aqueous solutions include USUN Bio Co., Jiangyin, Jiangsu Province, China.

Appropriate topical doses of MAPs and derivatives thereof are in the range of about 0.1 to about 50 $\mu$g/cm$^2$ of treated area, such as about 1 to about 20 $\mu$g/cm$^2$ of treated area, including about 2 to about 10 $\mu$g/cm$^2$ of treated area, such as about 5 $\mu$g/cm$^2$ of treated area.

Appropriate concentrations of montelukast in an aqueous solution product may be 0.1 to 10 mg/mL calculated as the free base, and appropriate pH values for such solutions are in the range of about 5.0 (e.g. about 7.0) to about 11.0 (for example about 5.5 (e.g. about 8.0) to about 10.0, such as about pH 9.0 or between about 5.5 to about 7.5), irrespective of whether the formulation employed is a combined preparation or a kit of parts as hereinbefore described.

Appropriate topical doses of montelukast and salts/solvates thereof are in the range of about 0.01 to about 50 (such as about 20, e.g. about 17.5, including about 10) $\mu$g/cm$^2$ of treated area, such as about 0.05 (e.g. about 0.1, including about 0.5) to about 17.5, including about 10, such as about 7.5, e.g. about 5) $\mu$g/cm$^2$ of treated area, in all cases calculated as the free base.

According to a further aspect of the invention, there is provided a pharmaceutical (e.g. liquid- or (e.g. aqueous) solution-based) formulation comprising montelukast or a pharmaceutically acceptable salt of solvate thereof, which formulation is suitable for, adapted for, and/or packaged and presented for, (a) topical administration (e.g. to the mucosa or, preferably, to the skin); and/or (b) the treatment of inflammation, an inflammatory disorder and/or a condition characterized by inflammation. Similarly, there is provided such a formulation for use in the treatment of inflammation, an inflammatory disorder and/or a condition characterized by inflammation (e.g. as a symptom) by way of direct topical administration of that formulation (e.g. to the mucosa or, preferably, to the skin).

In relation to this aspect of the invention, for the avoidance of doubt, topical formulations comprising montelukast may be used in any and all treatments of inflammation, in the treatment of any and all inflammatory disorder(s), and/or in the treatment of any and all condition(s) characterized by inflammation, as hereinbefore mentioned, defined or described. Similarly, topical formulations comprising montelukast (including combinations) that may be mentioned include any and all of those mentioned, defined or described hereinbefore. Any and all of the above relevant disclosures are hereby incorporated by reference in conjunction with this aspect of the invention.

Nevertheless, topical (e.g. liquid- or (e.g. aqueous) solution-based) formulations comprising montelukast or a pharmaceutically acceptable salt or solvate thereof, have been found to be particularly useful in wound recovery, and may alleviate pain (including aching) and, particularly, pruritis/itching that is associated with the wound itself and the wound healing process. We have also found that such topical montelukast formulations are particularly useful to prevent and/or suppress the exudation of body fluids from wounds, particularly during the acute inflammation stage, for example during the first 48 hours, after a burn or wound has been inflicted. This prevents the risk of infection, and other physiological reactions. We have in addition found that such topical montelukast formulations are particularly useful in the prevention and/or suppression of scarring and melanin pigmentation (vide supra), whether associated with wounds or otherwise.

Suitable peroral doses of montelukast that may be mentioned are in the range of about 0.25 mg to about 600 mg, such as about 0.4 mg to about 200 mg, preferably about 5 mg to about 100 mg, for example about 7 mg (e.g. about 8 mg) to about 25 mg (e.g. about 12 mg) per day, irrespective of whether the formulation employed is a combined preparation or a kit of parts as hereinbefore described.

In any event, in respect of either active ingredient, the dose administered to a mammal, particularly a human, in the context of the present invention should be sufficient to effect a therapeutic response in the mammal over a reasonable timeframe (as described hereinbefore). One skilled in the art will recognize that the selection of the exact dose and composition and the most appropriate delivery regimen will also be influenced by inter a/la the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

Wherever the word "about" is employed herein, for example in the context of amounts, such as concentrations and/or doses of active ingredients, molecular weights or pHs, it will be appreciated that such variables are approximate and as such may vary by ±10%, for example ±5% and preferably ±2% (e.g. ±1%) from the numbers specified herein. In this respect, the term "about 10%" means e.g. ±10% about the number 10, i.e. between 9% and 11%.

The combination of one or more MAP or derivative thereof and montelukast may demonstrate clear synergistic effects in biological and/or clinical tests.

The combination products/methods described herein may have the advantage that they enable the administration of a normally orally-administered antiinflammatory drug, montelukast, in a topical setting.

The combination products/methods described herein may also have the advantage that, in the treatment of the conditions mentioned hereinbefore, they may be more convenient for the physician and/or patient than, be more efficacious than, be less toxic than, have a broader range of activity than, be more potent than, produce fewer side effects than, or that it/they may have other useful pharmacological properties over, similar methods (treatments) known in the prior art for use in the treatment of inflammatory disorders or otherwise.

The invention is illustrated by the following examples, in which:

FIGS. 1 and 2 and present ELISA test results for various inflammatory markers obtained from exudates from air pouches induced in mice according to Examples 1 and 2, respectively, tested with various test compounds;

FIG. 3 illustrates burn scores for the healing over time of third degree burns induced in rats, treated with various test compounds;

FIGS. 4 and 5 present ELISA test results for various inflammatory markers obtained from exudates from air pouches induced in mice according to Examples 4 and 5, respectively;

EXAMPLES

Example 1

Air Pouch Model I

Figure 1:
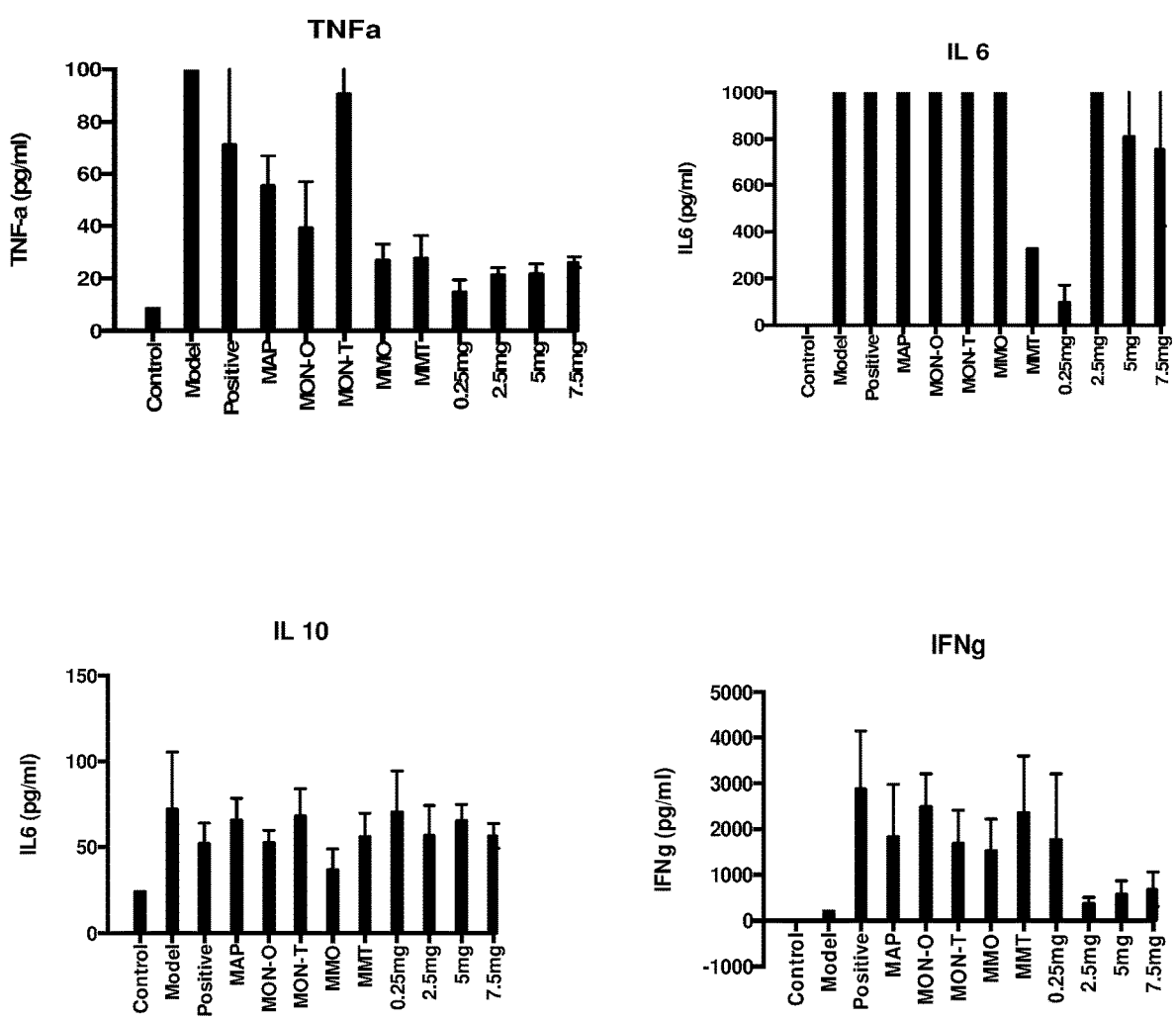

Healthy adult male C57BL/6 mice weighing between 20 and 30 g were supplied by Changzhou Cvens Experimental Animal Co. Ltd (Changzhou, Jiangsu Province, China). Prior to any experiments being conducted, mice were housed under standardized conditions (at a constant temperature or 22 t 2° C., with alternating 12 hour periods of light and darkness), and were fed on a standard mouse diet with water, for about a week.

General anesthesia was induced using intraperitoneal 3% chloral hydrate (Sinopharm Chemical Reagent Co., Ltd., Shanghai, China); 1 mL/10 g of body weight). The hair of the entire dorsum was shaved and depilated 1 day before sterile air injection.

Air pouches were produced by subcutaneous injection of sterile air (5 mL) into the intrascapular area of the mice. After three days, another injection of air (3 mL) was performed to maintain the pouches. In order to induce acute inflammation, three days after this final injection, animals received an injection of sterile carrageenan solution (CP Kelco, Taixing, Jiangsu Province, China; 1%, 0.5 mL; produced by adding 0.1 g of carrageenan powder into a beaker containing 10 mL of 0.9% saline solution and stirring). Mice were pre-treated with test samples or vehicle 1 hour before and 23 hours after the carrageenan injection into the subcutaneous air pouch. Animals were sacrificed 24 hours after the carrageenan injection.

Skin biopsies were taken from the air pouches. A part of the biopsy was fixed in formalin (produced by adding ultra pure water to 50 mL of a 40% formaldehyde solution (Nanchang Rain Dew Experimental Equipment Co., Ltd., Nanchang, Hubei Provence, China) up to a total volume of 500 mL) and analyzed by histological embedding in paraffin wax, sectioning and staining.

The cavity was washed with 4 mL of sterile phosphate buffer solution (pH 7.4; prepared by dissolving 4 g of NaCl, 0.1 g of KCl, 1.749 g of $Na_2HPO_4.12H_2O$ and 0.1 g of $KH_2PO_4$ in ultrapure water, adjusting the pH to 7.4 with HCl and diluting with water to a total volume of 500 mL).

Exudates were collected and volumes were quantified. The total number of cells was determined with a haematocytometer (ADVIA 2120 Hematology System, Siemens Healthineers). The exudates were centrifuged at 3000 rpm for 10 minutes at 4° C., and the supernatants were collected and stored at −20° C. for ELISA analysis using standard ELISA test kits (Biolegend™ from Dakewe Biotech Co., Beijing, China or Abcam™, Abcam (Shanghai) Trading Co. Ltd, China) and an ELISA reader (SH-1000 Hitachi, Japan) for tissue necrosis factor alpha (TNF-α), interleukin 1 beta (IL-1β), interleukin 6 (IL-6), interleukin 10 (IL-10), prostaglandin E2 (PGE2), interferon gamma (IFN-γ) and 5-hydroxytryptamine (5-HT; serotonin).

After conducting some preliminary experiments to validate the model, an experiment was conducted in which mice were treated by administering test samples or vehicle in accordance with Table 1 below.

In Table 1, MAP is a Mefp-1 solution, which is was prepared as follows. Blue mussels were harvested in the coastal area of Shandong Province, China. Mussel feet were collected, cut into small pieces and homogenized in an extraction buffer comprising 5% acetic acid in 4 mol/L of aqueous urea. The crude extracts were collected after centrifuging and then purified by liquid chromatography. The purified protein (semi-finished product; concentration 8 mg/mL; purity as measured by HPLC 91.72%; pH 4.2) was stored at 0° C. The solutions that were employed below were prepared by adding saline solution to this semi-finished product to obtain a concentration as described in Table 1. Montelukast sodium ("Mon"; MedChemExpress, Shanghai, China) and dexamethasone (MedChemExpress) were both obtained in powder form and dissolved in ultrapure water to obtain solutions with concentrations as described in Table 1. All the substances listed in Table 1 were administrated topically by directly injecting into the air pouches.

TABLE 1

| Group | No. Mice | Drug concn. (mg/mL) | Dose/mouse | Timing of Treatment (before carrageenan injection) |
| --- | --- | --- | --- | --- |
| Control (air injection only) | 6 | normal saline | 4.5 mg (of NaCl) | n/a |
| Model (carrageenan injection) | 6 | normal saline | 4.5 mg (of NaCl) | 1 hour |
| Positive (dexamethasone) | 6 | 0.4 | 200 μg | 1 hour |
| MAP | 6 | 3 | 1.5 mg | 1 hour |
| Mon (oral) | 6 | 1 | 200 μg | 1 hour |
| Mon (topical) | 6 | 0.4 | 200 μg | 1 hour |
| MAP + Mon (oral) | 6 | 3 (MAP) 1 (Mon) | 1.5 mg (MAP) 200 μg (Mon) | 1 hour (MAP) 1.5 hour (Mon) |
| MAP + Mon (topical) | 6 | 6 (MAP) 0.8 (Mon) | 1.5 mg (MAP) 200 μg (Mon) | 1 hour (MAP) 1.5 hour (Mon) |
| MAP 0.25 mg | 3 | 0.5 | 0.25 mg | 1 hour |
| MAP 2.5 mg | 3 | 5 | 2.5 mg | 1 hour |
| MAP 5 mg | 3 | 10 | 5 mg | 1 hour |
| MAP 7.5 mg | 3 | 15 | 7.5 mg | 1 hour |

The volume of the exudate and the weight of air pouch wall (±SD) for each group are tabulated in Table 2 below.

TABLE 2

| Group | Exudate volume (mL) | Pouch Wall Weight (g) |
| --- | --- | --- |
| Control | 3.33 ± 0.10 | 0.58 ± 0.06 |
| Model | 3.73 ± 0.12 | 0.81 ± 0.14 |
| Positive | 3.60 ± 0.14 | 0.72 ± 0.09 |
| MAP | 3.62 ± 0.12 | 0.66 ± 0.06 |
| Mon (oral) | 3.58 ± 0.15 | 0.67 ± 0.10 |
| Mon (topical) | 3.68 ± 0.15 | 0.66 ± 0.13 |

TABLE 2-continued

| Group | Exudate volume (mL) | Pouch Wall Weight (g) |
| --- | --- | --- |
| MAP + Mon (oral) | 3.53 ± 0.08 | 0.61 ± 0.12 |
| MAP + Mon (topical) | 3.60 ± 0.09 | 0.66 ± 0.07 |
| MAP 0.25 mg | 3.43 ± 0.12 | 0.85 ± 0.07 |
| MAP 2.5 mg | 3.60 ± 0.10 | 0.74 ± 0.04 |
| MAP 5 mg | 3.57 ± 0.15 | 0.69 ± 0.14 |
| MAP 7.5 mg | 3.6 ± 0.10 | 0.68 ± 0.15 |

The total cell count and classification ($\times 10^8$/mL) is tabulated in Table 3 below.

TABLE 3

| Group | Leukocyte | Neutrophil | Monocyte | Lymphocyte |
| --- | --- | --- | --- | --- |
| Control | 0.04 | 0.01 | 0.00 | 0.01 |
| Model | 5.06 | 0.28 | 0.10 | 4.57 |
| Positive | 2.48 | 0.22 | 0.05 | 2.08 |
| MAP | 2.71 | 0.23 | 0.10 | 2.24 |
| Mon (oral) | 2.38 | 0.21 | 0.07 | 1.98 |
| Mon (topical) | 3.82 | 0.29 | 0.17 | 3.22 |
| MAP + Mon (oral) | 1.53 | 0.21 | 0.06 | 1.16 |
| MAP + Mon (topical) | 1.65 | 0.19 | 0.11 | 1.27 |
| MAP 0.25 mg | 0.40 | 0.09 | 0.01 | 0.26 |
| MAP 2.5 mg | 1.26 | 0.18 | 0.05 | 0.94 |
| MAP 5 mg | 1.19 | 0.17 | 0.04 | 0.92 |
| MAP 7.5 mg | 1.65 | 0.27 | 0.07 | 1.22 |

The histological specimens were analysed and an inflammation score, an activity score (i.e. the number and density of neutrophils shown in pathological slides, indicating the degree of inflammation and, in the case of open wound and infective diseases, the degree of infection), an edema score and a fibroplastic proliferation score were estimated as follows.

The HE stained slices were observed under an optical microscope and were scored (1, 2 or 3 points) according to the perceived inflammation level (in cases showing only a small amount of inflammatory cells scattered in the area—1 point (mild); in cases where many inflammatory cells were observed—2 points (moderate); and, in cases with diffuse infiltration—3 points (severe)). A similar scoring system was employed for edema levels (3 points for most severe and 1 point for mild) after overall observation. Scores for neutrophils employed the same methodology as that employed for inflammatory cells.

TABLE 4

| Group | Inflammation score | Activity score | Edema Score | Sum | Fibroplastic proliferation score |
|---|---|---|---|---|---|
| Control | 0.67 | 0.50 | 1.00 | 3.00 | 0.83 |
| Model | 3.00 | 2.00 | 1.50 | 6.67 | 0.17 |
| Positive | 1.50 | 0.83 | 1.67 | 4.00 | 0.00 |
| MAP | 2.67 | 1.50 | 1.67 | 6.00 | 0.17 |
| Mon (oral) | 1.83 | 1.00 | 1.00 | 4.17 | 0.33 |
| Mon (topical) | 2.17 | 1.00 | 1.50 | 5.50 | 0.83 |
| MAP + Mon (oral) | 1.83 | 1.00 | 0.67 | 4.83 | 1.33 |
| MAP + Mon (topical) | 2.00 | 1.17 | 0.83 | 4.33 | 0.33 |
| MAP 0.25 mg | 2.00 | 1.33 | 1.00 | 5.00 | 0.67 |
| MAP 2.5 mg | 1.67 | 1.00 | 1.67 | 4.67 | 0.33 |
| MAP 5 mg | 2.00 | 1.00 | 1.67 | 5.00 | 0.33 |
| MAP 7.5 mg | 2.00 | 1.00 | 1.00 | 5.00 | 1.00 |

In the Control group, the pouch wall showed small amount of scattered inflammatory cell infiltration, rare neutrophil infiltration, mild edema, and mild fibrous tissue proliferation.

In the Model group, the pouch wall showed severe inflammatory cell infiltration in the whole layer (a large number of neutrophils), severe interstitial edema, and occasionally fibrous tissue proliferation.

In the Positive control group, the pouch wall showed mild to moderate inflammatory cell infiltration, occasionally infiltration in the whole layer, severe interstitial edema, and no fibrous tissue formation.

In the MAP (1.5 mg) group, the pouch wall showed severe inflammatory cell infiltration in the whole layer, moderate to severe interstitial edema, and occasionally fibrous tissue proliferation.

In the Mon (oral) group, the pouch wall showed moderate inflammatory cell infiltration, with a small amount of neutrophil infiltration, mild interstitial edema, and occasionally fibrous tissue proliferation.

In the Mon (topical) group, the pouch wall showed moderate to severe inflammatory cell infiltration, with a small amount of neutrophil infiltration, mild to moderate interstitial edema, and lightly fibrous tissue proliferation.

In the MAP+Mon (oral) group, the pouch wall showed moderate inflammatory cell infiltration, with a small amount of neutrophil infiltration, mild interstitial edema, and obvious fibrous tissue proliferation.

In the MAP+Mon (topical) group, the pouch wall showed moderate inflammatory cell infiltration, with a small amount of neutrophil infiltration, mild interstitial edema, and occasionally fibrous tissue proliferation.

In the MAP (0.25 mg) group, the pouch wall showed moderate inflammatory cell infiltration, with a small amount of neutrophil infiltration, mild interstitial edema, and mild fibrous tissue proliferation.

In the MAP (2.5 mg) group, the pouch wall showed moderate inflammatory cell infiltration, with a small amount of neutrophil infiltration, obvious interstitial edema, and occasionally fibrous tissue proliferation.

In the MAP (5 mg) group, the pouch wall showed moderate inflammatory cell infiltration, with a small amount of neutrophil infiltration, mild to moderate interstitial edema, and occasionally fibrous tissue proliferation.

In the MAP (7.5 mg) group, the pouch wall showed moderate inflammatory cell infiltration, with mild to moderate neutrophil infiltration, mild interstitial edema, and mild fibrous tissue proliferation.

The ELISA test results of the exudate showed PGE2 and 5-HT levels that were below detection ranges. The results for TNF-α, IL-6, IL-10 and IFN-γ (±SD) are tabulated in Table 5 below and are shown graphically in FIG. 1 (in respect of which, abbreviations are given in Table 5).

TABLE 5

| Group | TNF-α | IL-6 | IL-10 | IFN-γ |
|---|---|---|---|---|
| Control | 8.62 ± 0.10 | 2.3 ± 0.00 | 24.32 ± 0.00 | −5.00 ± 3.00 |
| Model | 674.65 ± 244.26 | 34050 ± 13984 | 72.13 ± 33.13 | 167 ± 44.48 |
| Positive | 71.31 ± 111.19 | 3649 ± 1764 | 52.33 ± 11.60 | 2879 ± 1267 |
| MAP | 55.45 ± 11.51 | 10411 ± 6948 | 65.79 ± 12.64 | 1842 ± 1129 |
| Mon (oral) (MON-O) | 39.41 ± 17.62 | 8453 ± 9758 | 52.59 ± 7.22 | 2495 ± 711 |
| Mon (topical) (MON-T) | 90.73 ± 109.02 | 2528 ± 1538 | 68.18 ± 15.81 | 1690 ± 725 |
| MAP + Mon (oral) (MMO) | 27.08 ± 6.14 | 2459 ± 681 | 37.06 ± 11.91 | 1534 ± 685 |
| MAP + Mon (topical) (MMT) | 27.87 ± 8.49 | 330 ± 0.00 | 56.24 ± 13.73 | 2362 ± 1233 |
| MAP 0.25 mg (0.25 mg) | 14.95 ± 4.54 | 98.7 ± 73.55 | 70.50 ± 23.86 | 1778 ± 1430 |
| MAP 2.5 mg (2.5 mg) | 21.53 ± 2.69 | 5289 ± 5575 | 56.64 ± 17.56 | 379.91 ± 138.01 |
| MAP 5 mg (5 mg) | 21.76 ± 3.84 | 811 ± 224.56 | 65.50 ± 9.33 | 575.66 ± 289.83 |
| MAP 7.5 mg (7.5 mg) | 26.23 ± 2.02 | 757 ± 331.78 | 56.51 ± 7.15 | 688.76 ± 374.80 |

Example 2

Air Pouch Model II

Following the same protocol as described in Example 1 above, a further comparative experiment was conducted in which mice (Comparative Medicine Centre, Yangzhou University, Jiangsu Province, China) were treated by administering test samples or vehicle in accordance with Table 6 below.

In Table 6, "Dex" is an abbreviation for dexamethasone and "Dopamine" is a 4 mg/mL aqueous solution of dopamine hydrochloride (Shanghai Aladdin Bio-Chem Technology Co., Ltd., Shanghai, China).

TABLE 6

| Group | No. Mice | Drug concn. (mg/mL) | Dose/mouse | Timing of Treatment (before carrageenan injection) |
|---|---|---|---|---|
| Control | 6 | normal saline | 4.5 mg (of NaCl) | n/a |
| Model | 6 | normal saline | 4.5 mg (of NaCl) | 1 hour |
| Dex | 6 | 0.8 | 400 µg | 1 hour |
| Dopamine | 6 | 4 | 2 mg | 1 hour |
| MAP | 6 | 0.5 | 250 µg | 1 hour |
| Mon + MAP | 6 | 0.4 (Mon) 1 (MAP) | 100 µg (Mon) 250 µg (MAP) | 1.5 hour (Mon) 1 hour (MAP) |
| Dex + MAP | 6 | 1.6 (Dex) 1 (MAP) | 400 µg (Dex) 250 µg (MAP) | 1.5 hour (Dex) 1 hour (MAP) |
| Mon | 6 | 0.2 | 100 µg | 1 hour |

The volume of the exudate and the weight of air pouch wall (means±SD) for each group are tabulated in Table 7 below.

TABLE 7

| Group | Exudate volume (mL) | Pouch Wall Weight (g) |
|---|---|---|
| Control | 2.57 ± 0.05 | 0.44 ± 0.02 |
| Model | 3.10 ± 0.21 | 0.62 ± 0.09 |
| Dex | 2.87 ± 0.06 | 0.45 ± 0.01 |
| Dopamine | 2.93 ± 0.06 | 0.44 ± 0.07 |
| MAP | 3.00 ± 0.10 | 0.49 ± 0.04 |
| Mon + MAP | 2.90 ± 0.10 | 0.53 ± 0.04 |
| Dex + MAP | 3.03 ± 0.06 | 0.48 ± 0.05 |
| Mon | 2.83 ± 0.15 | 0.52 ± 0.03 |

The total cell count and classification ($\times 10^6$/mL) is tabulated in Table 8 below.

TABLE 8

| Group | Leukocyte | Neutrophil | Monocyte | Lymphocyte |
|---|---|---|---|---|
| Control | 0.07 | 0.02 | 0.03 | 0.01 |
| Model | 2.33 | 0.14 | 2.08 | 0.05 |
| Dex | 0.88 | 0.13 | 0.67 | 0.03 |
| Dopamine | 1.91 | 0.19 | 1.58 | 0.05 |
| MAP | 1.74 | 0.19 | 1.40 | 0.06 |
| Mon + MAP | 1.00 | 0.18 | 0.69 | 0.05 |
| Dex + MAP | 1.06 | 0.16 | 0.77 | 0.05 |
| Mon | 1.58 | 0.26 | 1.15 | 0.07 |

The histological specimens were analysed and an inflammation score, an activity score and a fibroplastic proliferation score were estimated as in Example 1 above and are tabulated in Table 9 below.

TABLE 9

| Group | Inflammation score | Activity score | Edema Score | Sum | Fibroplastic proliferation score |
|---|---|---|---|---|---|
| Control | 0.50 | 0.00 | 1.00 | 1.50 | 0.67 |
| Model | 2.17 | 1.83 | 2.00 | 6.00 | 0.00 |
| Dex | 0.83 | 0.33 | 0.83 | 2.00 | 0.00 |
| Dopamine | 2.00 | 1.67 | 2.33 | 6.00 | 0.00 |
| MAP | 1.33 | 1.17 | 1.67 | 4.17 | 0.00 |
| Mon + MAP | 1.67 | 1.17 | 1.17 | 4.00 | 0.00 |
| Dex + MAP | 1.00 | 0.17 | 1.17 | 2.33 | 0.00 |
| Mon | 1.83 | 1.50 | 1.50 | 4.83 | 0.00 |

In the Control group, the pouch wall showed small amount of lymph cells infiltration, no neutrophil infiltration, partial mild to moderate edema, and mild fibrous tissue proliferation.

In the Model group, the pouch wall showed severe inflammatory cell infiltration in the whole layer, severe interstitial edema, and no fibrous tissue proliferation.

In the Dex group, the pouch wall showed small amount of lymph cells infiltration, occasionally light neutrophil infiltration, mild interstitial edema, and no fibrous tissue formation.

In the Dopamine group, the pouch wall showed a lot of inflammatory cell infiltration, mild to moderate interstitial edema, and no fibrous tissue proliferation.

In the MAP group, the pouch wall showed a lot of inflammatory cell infiltration, mild to moderate interstitial edema, and no fibrous tissue proliferation.

In the Mon+MAP group, the pouch wall showed moderate inflammatory cell infiltration, mild interstitial edema, and no fibrous tissue proliferation.

In the Dex+MAP group, the pouch wall showed small amount of scattered lymph cell infiltration, occasionally neutrophil infiltration, mild interstitial edema, and no fibrous tissue proliferation.

In the Mon group, the pouch wall showed a lot of inflammatory cell infiltration, mild to moderate interstitial edema, and no fibrous tissue proliferation.

Figure 2:
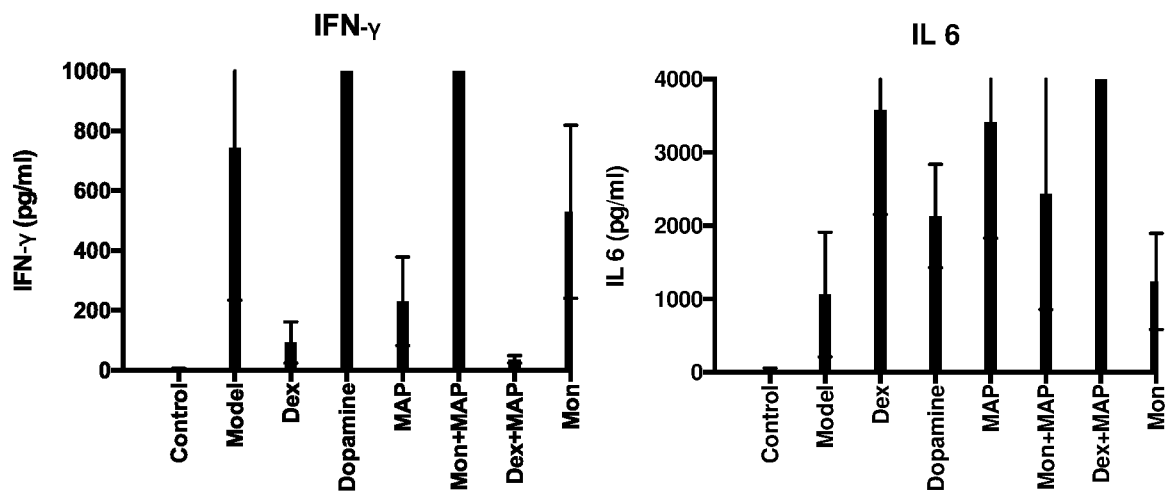

The ELISA test results of the exudate for TNF-α, IL-6, IL-10 and IFN-γ always showed stable, high responses with a similar variation tendency. The results for IL-6 and IFN-γ (±SD) are tabulated in Table 10 below and shown graphically in FIG. 2.

TABLE 10

| Group | IL-6 | IFN-γ |
|---|---|---|
| Control | 1083.94 ± 433.74 | −3.74 ± 1.3 |
| Model | 1213.54 ± 790.71 | 855.32 ± 570.36 |
| Dex | 3697.30 ± 5112.52 | 238.91 ± 272.27 |
| Dopamine | 1740.11 ± 765.02 | 5153.02 ± 5773.45 |
| MAP | 1686.11 ± 632.33 | 282.01 ± 192.24 |
| Mon + MAP | 1674.80 ± 696.85 | 1487.61 ± 815.47 |
| Dex + MAP | 8352.25 ± 6162.60 | 48.44 ± 35.58 |
| Mon | 1493.42 ± 564.77 | 896.90 ± 633.60 |

Example 3

Burn Injury Model

Healthy adult male Sprague-Dawley rats weighing between 200 and 300 g were supplied by Beijing Vital River Laboratory Animal Technology Co. Ltd, Beijing, China.

Prior to any experiments being conducted, rats were housed under standardized conditions (at a constant temperature or 22 t 2° C., with alternating 12 hour periods of light and darkness) and were fed on a standard rat diet with water.

Rats were anaesthetised with 3% chloral hydrate (Sinopharm Chemical Reagent Co., Ltd., Shanghai, China) (1 mL/100 g of body weight) administered by intraperitoneal injection. The dorsal trunk was of each rat was shaved with an electric razor and surgically prepared with 70% alcohol scrubs. A constant temperature and constant pressure scald instrument (YLS-5Q, Shandong Academy of Medical Sciences, China) was employed, as this allows for a precise measurement of pressure applied to the skin surface. Thermal injury was induced by heating a stylus (with a surface area of 4 cm$^2$) to 80° C. and applying the stylus to the surface of the skin for a contact time of 18 seconds. 500 grams of pressure was applied during the operation. In this way, four two-degree shallow to deep burn wounds were created on each rat. Test compounds or vehicle were applied to the surface of the wound.

Rats were kept in separate cages but were allowed to move freely throughout the test period. In the first treatment, 500 µL of the relevant solutions was applied about 3 to 4 hours after the surgery (Day 0) and then once daily for the next 7 days. Gross appearances of the scald wounds were observed every day. Photographs were taken at 48 hours (Day 2), and on the 4$^{th}$ (Day 4) and 7$^{th}$ (Day 7) days with a digital camera to compare wound healing. The skin lesions were evaluated for the following criteria: blistering, swelling, redness, crust, bleeding, secretion, granulation tissue and scar tissue. The degree of healing was expressed as the wound contraction ratio (WCR):

$$WCR = (A_0 - A_t)/A_0 \times 100\%$$

in which $A_0$ and $A_t$ refer to the initial area and the wound area at time t, respectively.

On Days 2, 4 and 7 after application of the burn, two rats were sacrificed and the burned skins excised. The freshly isolated skin was fixed in 10% neutral buffered formalin (which contained 4% of formaldehyde). This was used for histological embedding, staining and immunohistochemical studies.

Rats were treated by administering test samples or vehicle in accordance with the Table 11 below. Administered solutions were made up substantially as described in Example 1 above.

TABLE 11

| Group | Drug concn. (mg/mL) | Dosage/ wound |
|---|---|---|
| Control (i.e. untreated rats) | — | — |
| Saline | normal saline | 4.5 mg NaCl |
| Dexamethasone | 0.8 | 0.4 mg |
| MAP | 0.5 | 0.25 mg |
| Montelukast | 0.5 | 0.25 mg |
| MAP + dexamethasone | 1 (MAP) 1.6 (dexamethasone) | 0.25 mg (MAP) 0.4 mg (dexamethasone) |
| MAP + montelukast | 1 (for both) | 0.25 mg of each drug |

Results

Figure 3:
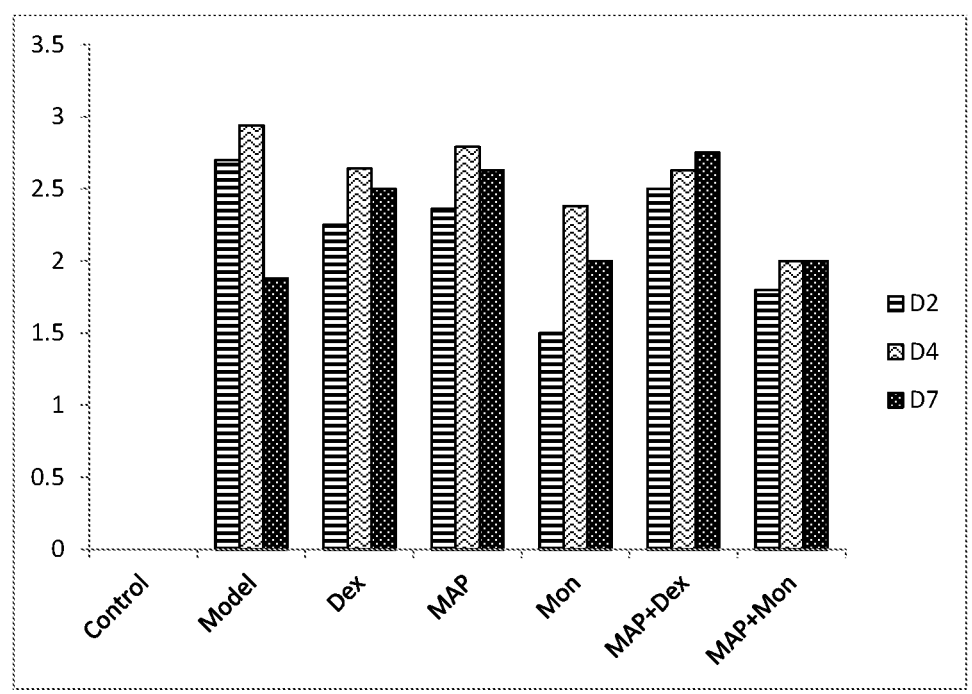

Burn scores are shown in Table 12 below and are illustrated in FIG. 3. Skin samples were sent to the Department of Pathology of Nanjing Hospital of Chinese Medicine, China. Samples were fixed and embedded, and histological sections were cut and stained. The stained sections were examined under a light microscope and pictures were taken. All pictures were interpreted and scored according to the following criteria: first degree—the epidermis was damaged and the substrate remains intact (score 1 point); superficial second degree—the epidermis was completely damaged and the papillary layer was damaged (1.5 points): deep second degree—the dermis was injured into the reticular layer and retain some dermis (2.5 points); and third degree—the dermis was completely damaged and the muscles and/or bones affected (3 points).

TABLE 12

| Group | Day 2 | Day 4 | Day 7 |
|---|---|---|---|
| Control | 0.00 | 0.00 | 0.00 |
| Saline (Model) | 2.70 | 2.94 | 1.88 |
| Dexamethasone (Dex) | 2.25 | 2.64 | 2.50 |
| MAP | 2.36 | 2.79 | 2.63 |
| Montelukast (Mon) | 1.50 | 2.38 | 2.00 |
| MAP + dexamethasone | 2.50 | 2.63 | 2.75 |
| MAP + montelukast | 1.80 | 2.00 | 2.00 |

Example 4

Air Pouch Model: Topical Administration Versus Oral Administration

An experiment was carried out, essentially as described in Example 1 (except that, in this case C57BL/16 mice were supplied by Nanjing Biomedical Research Institute of Nanjing University (NBRI)).

The experiment was conducted in which mice were treated by administering test samples or vehicle in accordance with Table 13 below. All substances listed in Table 13 were administrated topically by directly injecting into the air pouches, except for Mon (oral) (Mon-O), which was intragastric administrated.

TABLE 13

| Group | No. Mice | Drug concn. (mg/mL) | Dose/mouse | Timing of Treatment (before carrageenan injection) |
|---|---|---|---|---|
| Control (air injection only) | 6 | Normal saline | 4.5 mg (of NaCl) | n/a |
| Model (carrageenan injection) | 8 | Normal saline | 4.5 mg (of NaCl) | 1 hour |
| Positive (dexamethasone) | 6 | 0.4 | 200 µg | 1 hour |
| Mon-O | 8 | 0.4 | 200 µg | 1 hour |
| Mon-T | 8 | 0.4 | 200 µg | 1 hour |

The volume of the exudate and the weight of air pouch wall (means ± SD) for each group are tabulated in Table 14 below.

TABLE 14

| Group | Exudate volume (mL) | Pouch Wall Weight (g) |
|---|---|---|
| Control | 3.48 ± 0.12 | 0.68 ± 0.07 |
| Model | 3.76 ± 0.05 | 0.72 ± 0.09 |
| Positive | 3.3 ± 0.15 | 0.63 ± 0.09 |
| Mon-O | 3.69 ± 0.14 | 0.68 ± 0.08 |
| Mon-T | 3.54 ± 0.09 | 0.65 ± 0.06 |

The total cell count and classification ($\times 10^6$/mL) is tabulated in Table 15 below.

TABLE 15

| Group | Leukocyte | Neutrophil | Monocyte |
|---|---|---|---|
| Control | 0.09 | 8.75 | 0.00 |
| Model | 3.34 | 260.03 | 74.17 |
| Positive | 3.49 | 285.97 | 62.53 |
| Mon-O | 2.66 | 216.89 | 46.81 |
| Mon-T | 2.19 | 170.98 | 42.10 |

Histological specimens were analyzed and an inflammation score, an activity score, an edema score and a fibroblast proliferation score were estimated largely as described in Example 1 above, and are shown in Table 16 below.

TABLE 16

| Group | Inflammation Score | Edema Score | Activity score | Sum |
|---|---|---|---|---|
| Control | 0.33 | 1.17 | 0.00 | 1.50 |
| Model | 2.17 | 2.67 | 1.17 | 6.00 |
| Positive | 1.83 | 1.67 | 0.67 | 4.17 |
| Mon-O | 2.33 | 2.17 | 1.67 | 6.17 |
| Mon-T | 2.00 | 1.50 | 1.00 | 4.50 |

In the Control group, the pouch wall showed a small amount of scattered inflammatory cells infiltration, mild edema and no obvious neutrophil infiltration.

In the Model group, the pouch wall showed moderate to severe chronic inflammatory cell infiltration in the whole layer, moderate to severe edema and scattered neutrophil infiltration.

In the Positive control group, the pouch wall showed moderate chronic inflammatory cell infiltration, moderate interstitial edema and a small amount of neutrophil infiltration.

In the Mon-O group, the pouch wall showed moderate to severe chronic inflammatory cell infiltration in the whole layer, and moderate to severe edema.

In the Mon-T group, the pouch wall showed moderate chronic inflammatory cell infiltration, mild to moderate edema, and a small amount of neutrophil infiltration.

Figure 4:
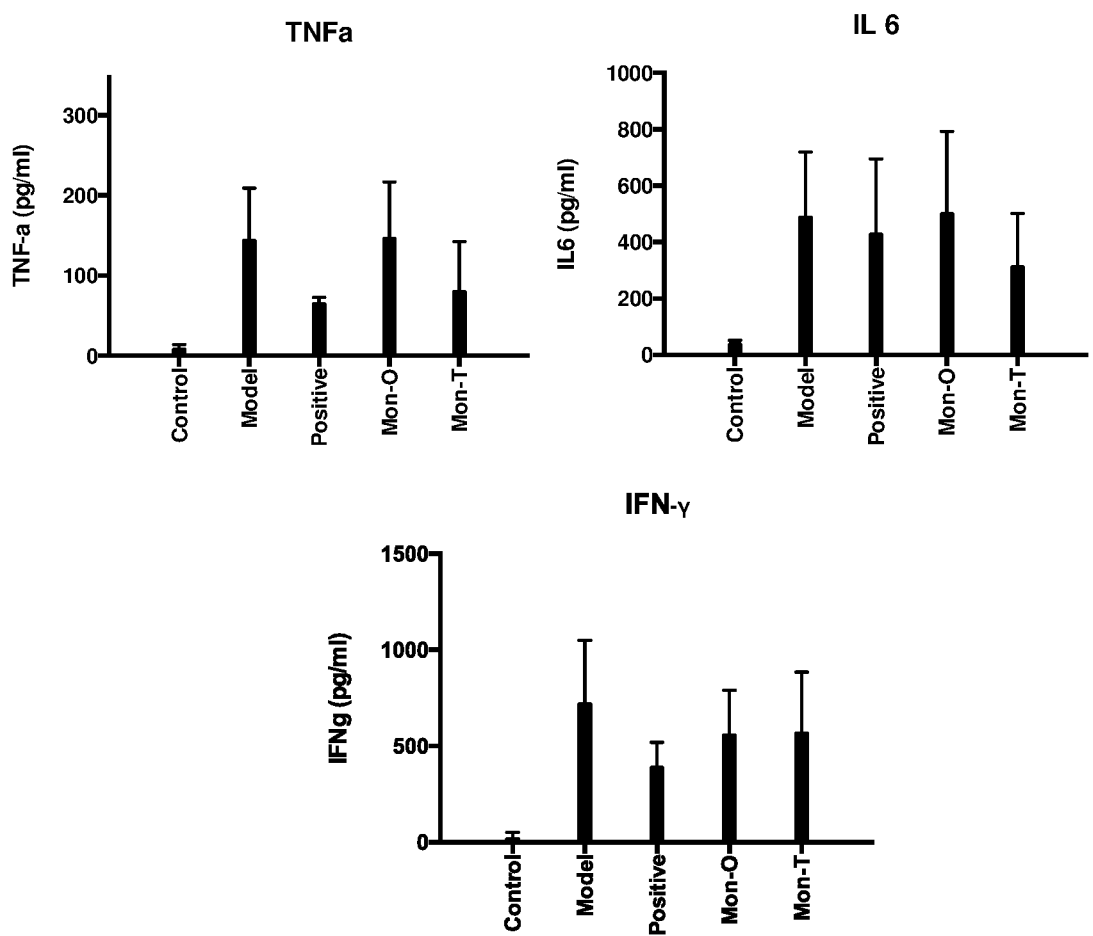

The ELISA test results of the exudate for TNF-α, IL-6, IL-10 and IFN-γ always showed stable, high responses with a similar variation tendency. The results for TNF-α, IL-6 and IFN-γ (±SD) are tabulated in Table 17 below and shown graphically in FIG. 4.

TABLE 17

| Group | TNF-α | IL-6 | IFN-γ |
|---|---|---|---|
| Control | 8.42 ± 5.65 | 36.95 ± 14.22 | 18.34 ± 33.65 |
| Model | 143.60 ± 65.56 | 487.97 ± 231.99 | 718.51 ± 331.12 |
| Positive | 65.08 ± 7.70 | 428.05 ± 267.27 | 388.83 ± 130.02 |
| Mon-O | 146.3 ± 70.74 | 500.25 ± 292.84 | 557.95 ± 231.86 |
| Mon-T | 80.37 ± 61.72 | 312.05 ± 189.23 | 568.19 ± 316.70 |

Example 5

Air Pouch Model: Combination of Montelukast

Following the same protocol as described in Example 1 above, a further comparative experiment was conducted in which mice (supplied by Changzhou Cvens Experimental Animal Co. Ltd.) were treated by administering test samples or vehicle in accordance with Table 18 below.

TABLE 18

| Group | No. Mice | Drug concn. (mg/mL) | Dose/mouse | Timing of Treatment (before carrageenan injection) |
|---|---|---|---|---|
| Control (air injection only) | 6 | Normal saline | 4.5 mg (of NaCl) | n/a |
| Model (carrageenan injection) | 6 | Normal saline | 4.5 mg (of NaCl) | 1 hour |
| Positive (dexamethasone) | 6 | 0.4 | 200 µg | 1 hour |

TABLE 18-continued

| Group | No. Mice | Drug concn. (mg/mL) | Dose/mouse | Timing of Treatment (before carrageenan injection) |
|---|---|---|---|---|
| MAP | 6 | 3 | 1.5 mg | 1 hour |
| MON-O | 6 | 1 | 200 µg | 1 hour |
| MON-T | 6 | 0.4 | 200 µg | 1 hour |
| MAP + Mon (oral) (MMO) | 6 | 3 (MAP) 1 (Mon) | 1.5 mg (MAP) 200 µg (Mon) | 1 hour (MAP) 1.5 hour (Mon) |
| MAP + Mon (topical) (MMT) | 6 | 6 (MAP) 0.8 (Mon) | 1.5 mg (MAP) 200 µg (Mon) | 1 hour (MAP) 1.5 hour (Mon) |

The volume of the exudate and the weight of air pouch wall (means±SD) for each group are tabulated in Table 19 below.

TABLE 19

| Group | Exudate volume (mL) | Pouch Wall Weight (g) |
|---|---|---|
| Control | 3.33 ± 0.10 | 0.58 ± 0.06 |
| Model | 3.73 ± 0.12 | 0.81 ± 0.14 |
| Positive | 3.60 ± 0.14 | 0.72 ± 0.09 |
| MAP | 3.62 ± 0.12 | 0.66 ± 0.06 |
| MON-O | 3.58 ± 0.15 | 0.67 ± 0.10 |
| MON-T | 3.68 ± 0.15 | 0.66 ± 0.13 |
| MMO | 3.53 ± 0.08 | 0.61 ± 0.12 |
| MMT | 3.60 ± 0.09 | 0.66 ± 0.07 |

The total cell count and classification ($\times 10^6$/mL) is tabulated in Table 20 below.

TABLE 20

| Group | Leukocyte | Neutrophil | Monocyte | Lymphocyte |
|---|---|---|---|---|
| Control | 0.04 | 0.01 | 0.00 | 0.01 |
| Model | 5.06 | 0.28 | 0.10 | 4.57 |
| Positive | 2.48 | 0.22 | 0.05 | 2.08 |
| MAP | 2.71 | 0.23 | 0.10 | 2.24 |
| MON-O | 2.38 | 0.21 | 0.07 | 1.98 |
| MON-T | 3.82 | 0.29 | 0.17 | 3.22 |
| MMO | 1.53 | 0.21 | 0.06 | 1.16 |
| MMT | 1.65 | 0.19 | 0.11 | 1.27 |

Histological specimens were analyzed and an inflammation score, an activity to score, an edema score and a fibroblast proliferation score were estimated as described in Example 1 above, and are shown in Table 21 below.

TABLE 21

| Group | Inflammation score | Activity score | Edema Score | Sum | Fibroblast proliferation score |
|---|---|---|---|---|---|
| Control | 0.67 | 0.50 | 1.00 | 3.00 | 0.83 |
| Model | 3.00 | 2.00 | 1.50 | 6.67 | 0.17 |
| Positive | 1.50 | 0.83 | 1.67 | 4.00 | 0.00 |
| MAP | 2.67 | 1.50 | 1.67 | 6.00 | 0.17 |
| MON-O | 1.83 | 1.00 | 1.00 | 4.17 | 0.33 |
| MON-T | 2.17 | 1.00 | 1.50 | 5.50 | 0.83 |
| MMO | 1.83 | 1.00 | 0.67 | 4.83 | 1.33 |
| MMT | 2.00 | 1.17 | 0.83 | 4.33 | 0.33 |

In the Control group, the pouch wall showed small amount of scattered inflammatory cell infiltration, rare neutrophil infiltration, mild edema, and mild fibrous tissue proliferation.

In the Model group, the pouch wall showed severe inflammatory cell infiltration in the whole layer (a large number of neutrophils), severe interstitial edema, and occasionally fibrous tissue proliferation.

In the Positive control group, the pouch wall showed mild to moderate inflammatory cell infiltration, occasionally infiltration in the whole layer, severe interstitial edema, and no fibrous tissue formation.

In the MAP (1.5 mg) group, the pouch wall showed severe inflammatory cell infiltration in the whole layer, moderate to severe interstitial edema, and occasionally fibrous tissue proliferation.

In the MON-O group, the pouch wall showed moderate inflammatory cell infiltration, with a small amount of neutrophil infiltration, mild interstitial edema, and occasionally fibrous tissue proliferation.

In the MON-T group, the pouch wall showed moderate to severe inflammatory cell infiltration, with a small amount of neutrophil infiltration, mild to moderate interstitial edema, and lightly fibrous tissue proliferation.

In the MMO group, the pouch wall showed moderate inflammatory cell infiltration, with a small amount of neutrophil infiltration, mild interstitial edema, and obvious fibrous tissue proliferation.

In the MMT group, the pouch wall showed moderate inflammatory cell infiltration, with a small amount of neutrophil infiltration, mild interstitial edema, and occasionally fibrous tissue proliferation.

Figure 5:
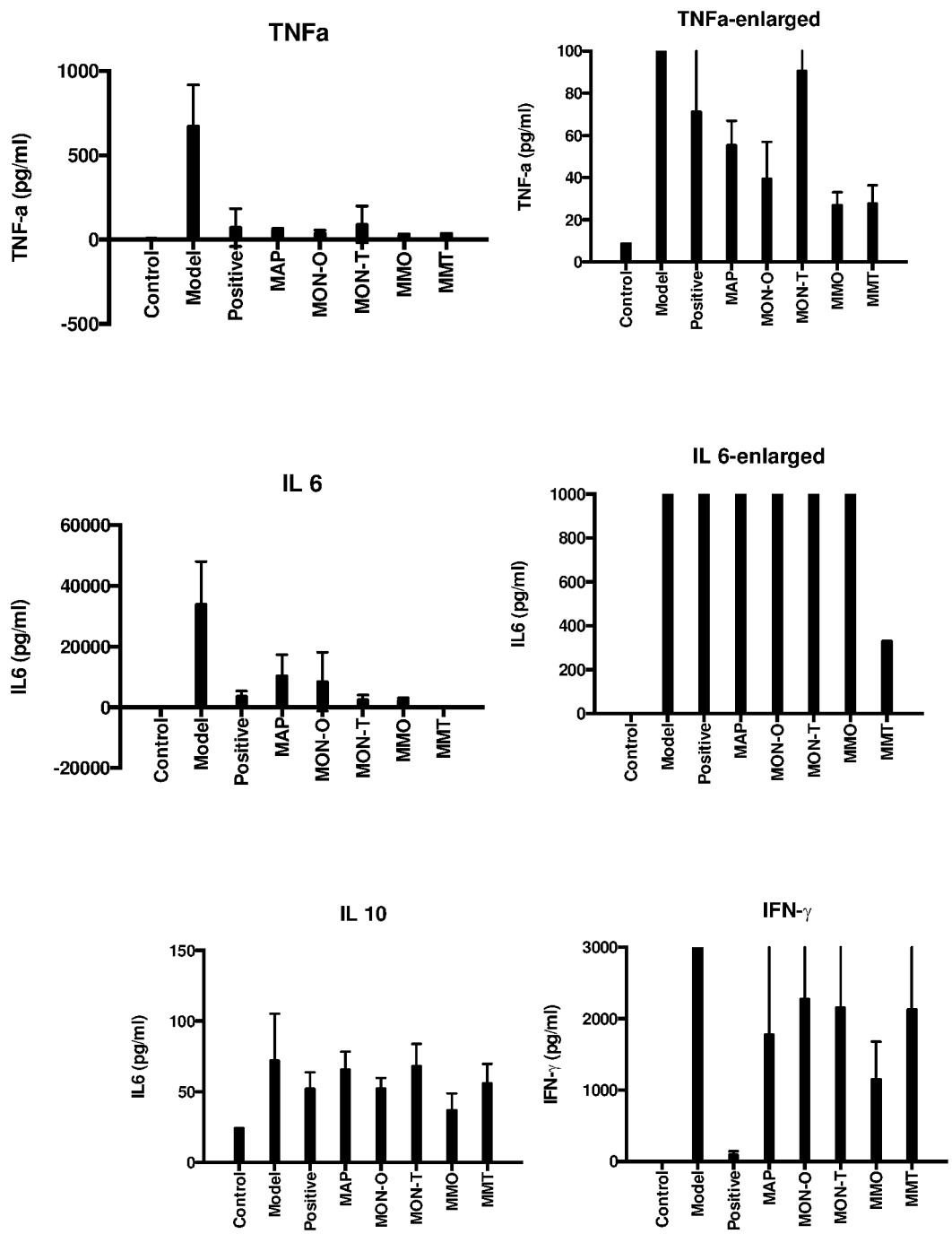

The ELISA test results of the exudate showed PGE2 and 5-HT levels that were below detection ranges. The results for TNF-α. IL-6, IL-10 and IFN-γ (±SD) are tabulated in Table 22 below and are shown graphically in FIG. 5.

TABLE 22

| Group | TNF-α | IL-6 | IL-10 | IFN-γ |
|---|---|---|---|---|
| Control | 8.62 ± 0.10 | 2.3 ± 0.00 | 24.32 ± 0.00 | −5.00 ± 3.00 |
| Model | 674.65 ± 244.26 | 34050 ± 13984 | 72.13 ± 33.13 | 167 ± 44.48 |
| Positive | 71.31 ± 111.19 | 3649 ± 1764 | 52.33 ± 11.60 | 2879 ± 1267 |
| MAP | 55.45 ± 11.51 | 10411 ± 6948 | 65.79 ± 12.64 | 1842 ± 1129 |
| Mon (oral) | 39.41 ± 17.62 | 8453 ± 9758 | 52.59 ± 7.22 | 2495 ± 711 |
| Mon (topical) | 90.73 ± 109.02 | 2528 ± 1538 | 68.18 ± 15.81 | 1690 ± 725 |
| MMO | 27.08 ± 6.14 | 2459 ± 681 | 37.06 ± 11.91 | 1534 ± 685 |
| MMT | 27.87 ± 8.49 | 330 ± 0.00 | 56.24 ± 13.73 | 2362 ± 1233 |

Example 6

Acute Wound Model 6-8 weeks old male C57BL/6 mice were supplied by Changzhou Cvens Experimental Animal Co. Ltd. Prior to any experiments being conducted, mice were housed under standardized conditions (at a constant temperature or 22±2° C., with alternating 12 hour periods of light and darkness), and were fed on a standard mouse diet with water, for about a week.

General anesthesia was induced using intraperitoneal 3% chloral hydrate (Sinopharm Chemical Reagent Co., Ltd., Shanghai, China; 1 mL/10 g of body weight). The hair on the back was shaved by a baby hair shaver and depilated with cream. Wiped the skin area and sterilized with 75% alcohol 2 times;

EMS skin biopsy punch (Electron Microscopy Sciences, P.O. Box 550, 1560 industry Road, Hatfield, Pa. 19440) with 0.6 mm diameter was used to make two round wounds on each side of the midline of the back. Full thickness skin was removed and the depth reached the fascia. The wounds left open without suture.

Different drugs were administered topically at 20 μL/wound, once daily from Day 0 to Day 12. The model group was given same amount of normal saline. There were 6 groups including 54 mice in this experiment shown in Table 23. Recombinant Human Epidermal Growth Factor (rhEGF, Shanghai Haohai Biological Technology Co. Ltd, Shanghai, China) was purchased and prepared according to the manufacturer's instructions. Lyophilized rhEGF powder (100000 IU/vial) was dissolved in 20 mL of normal saline to make a solution with a 5000 IU/mL concentration. The working dose of rhEGF for this experiment was 100 IU/wound. Montelukast sodium ("Mon"; MedChemExpress, MCE China, Shanghai, China) was obtained in a powder form and was dissolved in ultrapure water to obtain solutions with concentrations as described in Table 22 (L, M and H indicate low, medium and high montelukast doses, respectively)

Wounds were wrapped up with transparent dresser after drug administration.

Photographs were taken for each wound every other day from Day 0. Photos were scanned into a computer, and wound areas calculated using ImageJ image analysis software (National Institutes of Health, China).

The unhealed wound area was expressed as a percentage of the original wound area:

$A_t/A_0 \times 100\%$, where $A_0$ and $A_t$ refer to the initial area at Day 0 and the wound area at the date of measurement (time t), respectively.

Samples were taken at Day 3, Day 7 and Day 12 post wound-wound infliction. The mice were sacrificed and wound tissue of an area 1.8 cm×2.5 cm was removed. Half of the tissue was preserved in 10% neutral buffered formalin (Nanchang Rain Dew Experimental Equipment Co., Ltd., Nanchang, Hubei Provence, China), and analyzed by histological embedding in paraffin wax, sectioning and staining. HE and Masson stained paraffin sections were analyzed under an optical microscope. Skin regeneration, fibroblastic proliferation, collagen regeneration scores and inflammation scores were estimated.

The rest of the samples were stored at −80° C. for further analysis. Tissue was cut into small pieces and liquid nitrogen was added to increase brittleness. 9 mL of normal saline was added to 1 g of tissue, which was then ground using a Tissuelyser (Shanghai Jingxin Industrial Development Co., Ltd., Shanghai, China) at 55 Hz for 60 seconds, followed by centrifuging at 8000 rpm for 10 minutes at 4° C.

The supernatant was collected, and the extracted protein was used for ELISA analysis using standard ELISA test kits and an ELISA reader (SH-1000 Hitachi, Japan). Tissue necrosis factor alpha (TNF-α), interleukin 1 beta (IL-1β) and interleukin 6 (IL-6), vascular endothelial growth factor (VEGF) and hydroxyproline (Hyp) were assayed. The ELISA kits were purchased from Beijing 4A Biotech Co., Ltd. (Beijing, China).

Figure 6:
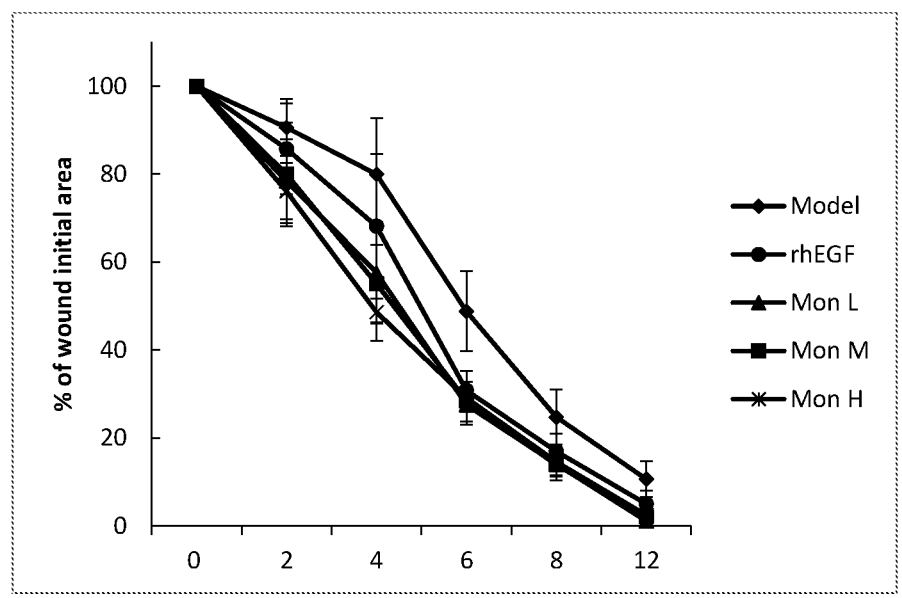
FIG. 6 shows the effect of montelukast on wound healing in an acute wound model of Example 6.

The effect of montelukast on wound healing were show in Table 24 below (where the numbers indicate the percentage of remaining wound area versus the initial wound at various time points in the different groups (±SD; n=5), and in FIG. 6.

TABLE 23

| GROUP | Day 3 | Day 7 | Day 12 | Total | MEANING | DOSAGE |
|---|---|---|---|---|---|---|
| Control | 3 | 4 | 2 | 9 | saline | / |
| Model | 3 | 4 | 2 | 9 | Model + saline | / |
| rhEGF | 3 | 4 | 2 | 9 | Model + rhEGF | 100 IU/wound |
| Mon L | 3 | 4 | 2 | 9 | Model + Mon L | 50 μg/wound |
| Mon M | 3 | 4 | 2 | 9 | Model + Mon M | 100 μg/wound |
| Mon H | 3 | 4 | 2 | 9 | Model + Mon H | 200 μg/wound |

TABLE 24

| Group | Model | rhEGF | Mon L | Mon M | Mon H |
|---|---|---|---|---|---|
| Day 2 | 90.58 ± 6.48 | 85.73 ± 10.29 | 78.41 ± 9.51 | 79.97 ± 11.79 | 76.11 ± 6.40 |
| Day 4 | 79.97 ± 12.74 | 68.15 ± 16.47 | 57.59 ± 11.54 | 55.09 ± 8.83 | 48.60 ± 6.49 |
| Day 6 | 48.79 ± 9.10 | 30.85 ± 1.87 | 27.53 ± 3.76 | 28.51 ± 1.03 | 29.13 ± 6.16 |
| Day 8 | 24.76 ± 6.29 | 16.93 ± 4.03 | 14.08 ± 2.85 | 13.87 ± 3.51 | 14.59 ± 3.04 |
| Day 12 | 10.66 ± 4.13 | 5.02 ± 3.03 | 1.15 ± 2.29 | 2.15 ± 3.73 | 2.48 ± 3.43 |

The above data show that montelukast had a significant effect on wound healing. At Day 4, the improvement rate in the Mon H group was about 39%.

Figure 7:
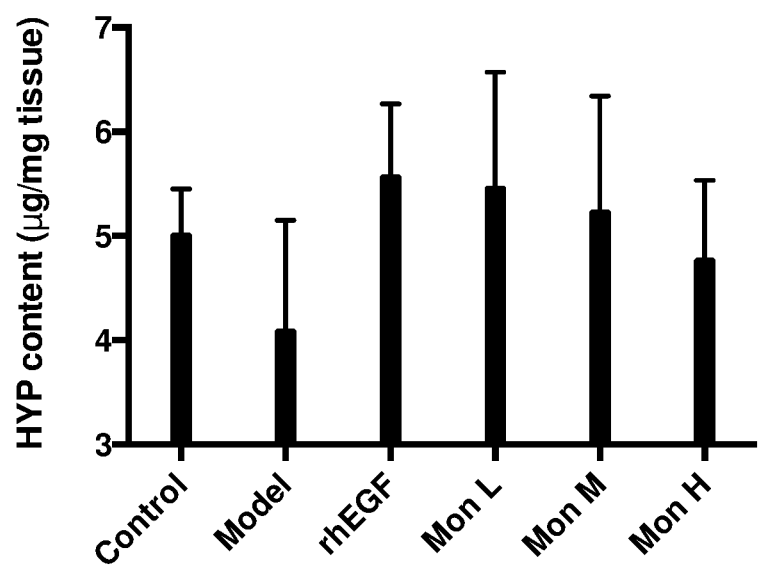
FIG. 7 shows wound hydroxyproline content in samples in the Example 6 model.

The wound HYP (µg/mg) content in samples, which is an indicator of collagen regeneration, is shown in Table 25 below and in FIG. 7.

TABLE 25

| | Hyp content (µg/mg tissue weight) | | | | Mean (n = 4) | SD |
|---|---|---|---|---|---|---|
| Control | 4.43 | 5.06 | 5.50 | 5.03 | 5.01 | 0.44 |
| Model | 5.40 | 2.82 | 3.89 | 4.25 | 4.09 | 1.06 |
| RhEGF | 6.54 | 4.89 | 5.39 | 5.45 | 5.57 | 0.70 |
| Mon L | 4.65 | 4.41 | 6.71 | 6.05 | 5.46 | 1.11 |
| Mon M | 4.94 | 4.18 | 6.80 | 4.98 | 5.23 | 1.11 |
| Mon H | 4.62 | 5.83 | 3.99 | 4.64 | 4.77 | 0.77 |

Example 7

Diabetic Wound Model

A similar experiment with essentially the same protocol to that described in Example 6 above was carried out on 8 to 12 week-old male db/db mice (C57BL/KsJ-db/db, with a body weight of 35-45 g/mouse; supplied by Changzhou Cvens Experimental Animal Co. Ltd.).

An EMS skin biopsy punch with a 0.8 mm diameter was used to make wounds.

Different drugs were administered topically at 20 µL/wound, once daily from Day 0 to Day 18. The model group was given same amount of normal saline. There were 3 groups including 39 mice in this experiment shown in Table 26 below.

TABLE 26

| GROUP | Day 6 | Day 12 | Day 18 | Tot. | MEANING | DOSAGE |
|---|---|---|---|---|---|---|
| Model | 4 | 8 | 1 | 13 | Model + saline | / |
| rhEGF | 4 | 8 | 1 | 13 | Model + rhEGF | 100 IU/each |
| Mon | 4 | 8 | 1 | 13 | Model + Mon | 100 µg/each |

Samples were taken on Day 6, Day 12 and Day 18 post-wound inflictions.

Figure 8:
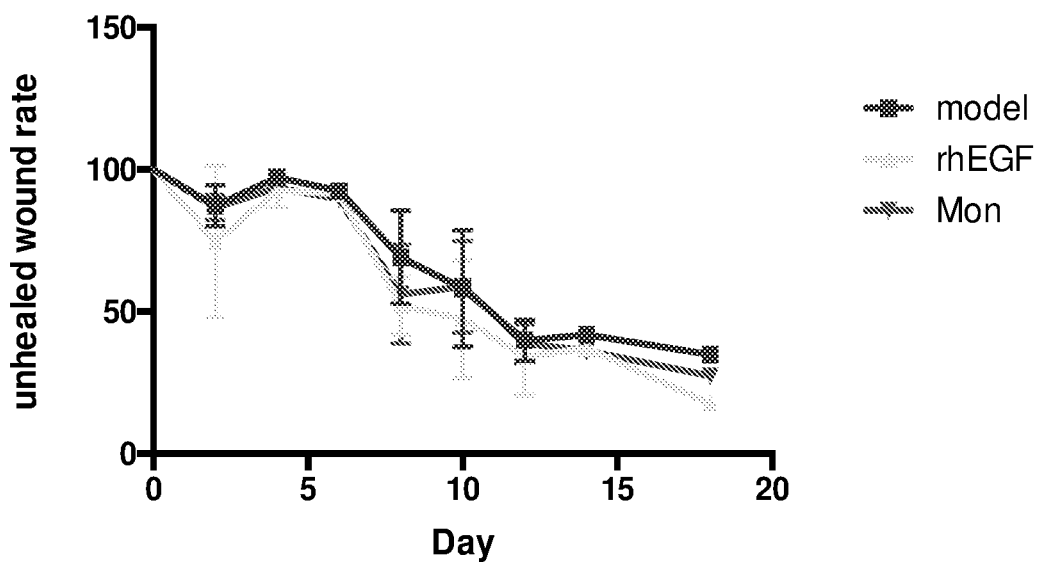
FIG. 8 shows the effect of montelukast on wound healing in a diabetic wound model of Example 7.

The effect of montelukast on wound healing are show in FIG. 8.

Figure 9:
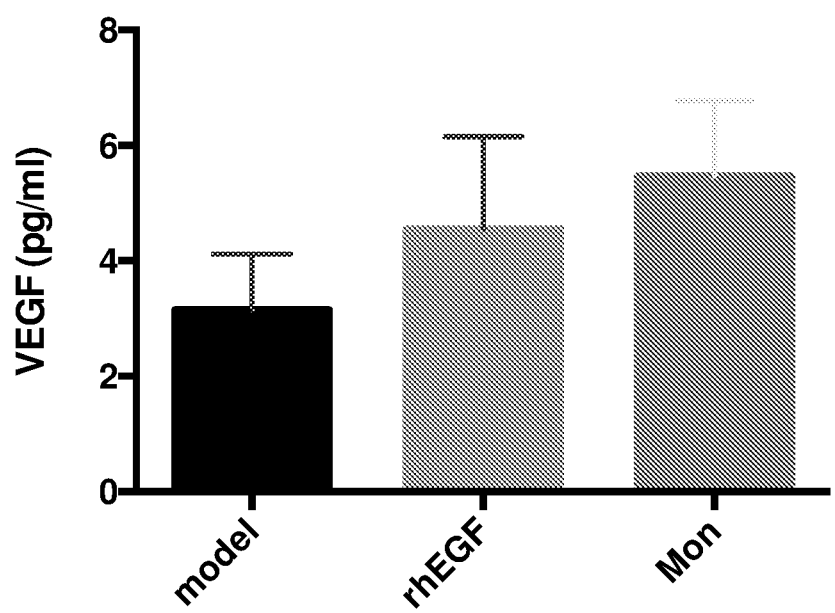
FIG. 9 shows wound vascular endothelial growth factor content (pg/g) in samples at Day 6 in the Example 7 model.

The result for VEGF content (pg/g) at Day 6 are tabulated in Table 27 below and are shown graphically in FIG. 9.

TABLE 27

| | | Model | rhEGF | Mon |
|---|---|---|---|---|
| VEGF | Mean | 3.15 | 4.55 | 5.47 |
| | SD | 0.97 | 1.60 | 1.31 |

The result showed that montelukast has increased the VEGF production in the wounded tissue for about 74% In comparison with that in model group.

Histological specimens were analyzed and skin regeneration, fibroblast proliferation, collagen regeneration scores (Masson score) and inflammation scores were estimated as follows.

The HE and Masson stained slices were observed under an optical microscope and were scored (1, 2 or 3 points) according to the following criteria. Skin regeneration score was 1 point when the newly generated skin covered area was no more than one third of the wound area; the score was 2 points when the newly generated skin covered an area greater than one third but less than two thirds of the wound area; and the score was 3 points when the newly generated skin covered area was at least two thirds of the wound area.

Fibroblast proliferation was scored as the following criteria:

| Fibroblast proliferation score | |
|---|---|
| Collagen fiber hyperplasia | Score |
| Myofibroblastic proliferation | 1 |
| proliferation of fibrous tissue | 2 |
| Collagen appeared between the fibrous tissues | 3 |

Inflammation was scored as the following criteria:

| Inflammation score | |
|---|---|
| Inflammatory cell infiltration | Score |
| Occasional | 0 |
| Sporadic | 1 |
| Manifest | 2 |
| Diffuse infiltration | 3 |

Collagen deposition score criterion for the Masson stained sample were as follows. A comparison was made with normal tissue. No clear blue staining was given 0 points;

blue fiber appearing in a scattered pattern was scored as 1 points; if more blue fiber appeared, this was scored as 2 points, and a diffuse blue colour was given 3 points.

Figure 10:
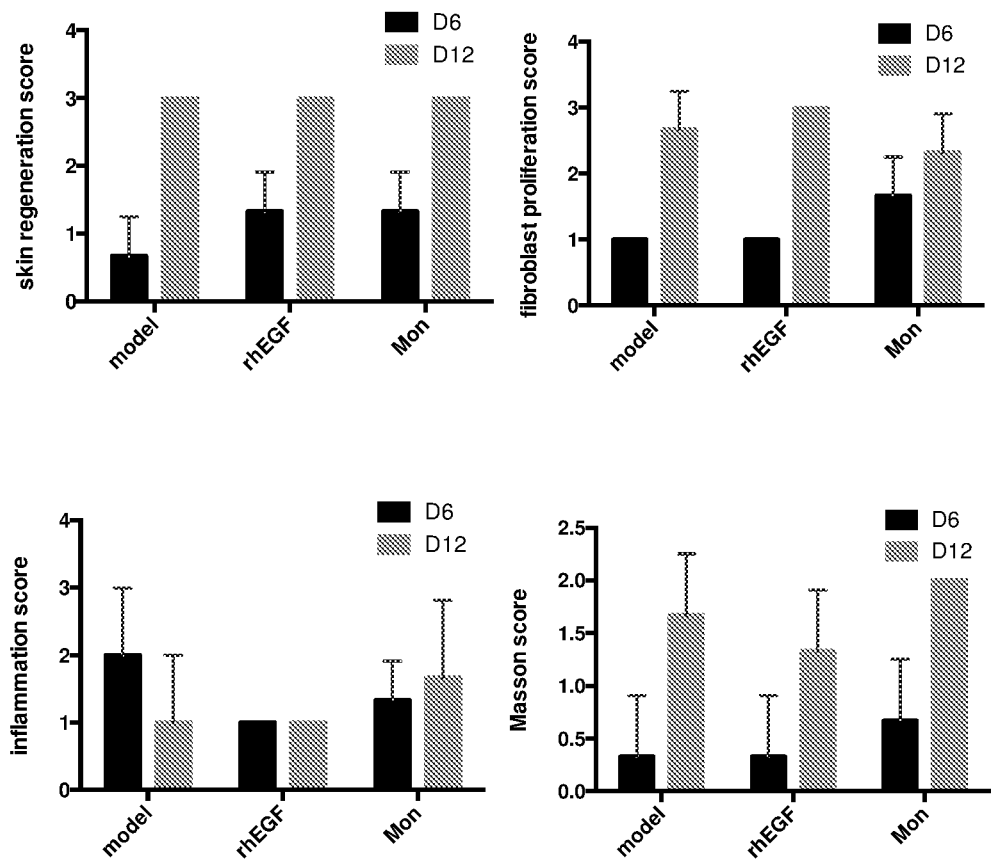
FIG. 10 shows the results of a histopathological analysis in samples at Days 6 and 12 in the Example 7 model.

The results of histopathological analysis are shown in FIG. 10.

The results shown that montelukast had the effects on accelerating wound healing, especially at an early stage following wound infliction.

Example 8

Montelukast Cream I

A cream based on montelukast sodium was made, consisting of the following components: montelukast sodium (200 mg; Arromax Pharmatech Co., Ltd, Suzhou, China), stearic acid (2 g), glycerin monostearate (2 g), hexadecanol (2 g), glycerin (5 g) and sodium hydroxide (0.25 g) (all Sinopharm Chemical Reagent Co. Ltd, Shanghai, China); ammonium acryloyldlmethyltaurateNP copolymer (0.13 g; Clariant Chemical (Guangzhou) Co., Ltd., Guangzhou, China); phenoxyethanol (0.3 g) and ethylhexyl glycerin (0.1 g) (both Shanghai Rayson Chemicals Co., Ltd., Shanghai, China); and purified water (88.42 g).

The stearic acid, glycerin monostearate and hexadecanol were mixed and heated to 85° C. with stirring until the mixture melted completely.

The ammonium acryloyldimethyltaurate/VP copolymer, purified water and sodium hydroxide were mixed with stirring at 85° C. to form a homogenous colloidal suspension.

Montelukast sodium, glycerin, phenoxyethanol and ethylhexyl glycerin were then combined with stirring until the montelukast completely dissolved.

The copolymer/water mixture was added to the stearic acid-containing mixture, which was emulsified by stirring quickly for five minutes using emulfication equipment. The resultant emulsion was cooled to 55° C., the montelukast-containing mixture was added with mixing. The resultant mixture was allowed to cool to room temperature to obtain the finished product.

Example 9

Montelukast Cream II

A similar procedure to that described in Example 8 above was followed to produce a second cream.

On this occasion, stearic acid (2 g) and glycerin monostearate (2 g) were heated first to 85° C. with stirring until the mixture melted completely; then polysorbate 80 (1 g; Sinopharm Chemical Reagent Co. Ltd) and sodium hyaluronate (0.4 g; Shandong Focuschem Biotech Co., Ltd, Shandong, China) were mixed together with purified water at 85° C. until the sodium hyaluronate was fully swelled.

These two mixtures were combined, emulsified and stirred, followed by cooling to 55° C., and then the same montelukast-containing mixture (as described in Example 8 above) was added with mixing. Cooling to room temperature gave the finished product.

Example 10

Montelukast Cream III

A similar procedure to that described in Example 8 above was followed to produce a third cream.

On this occasion, sorbitan monostearate (0.6 g), polysorbate 80 (1 g), hexadecanol (2 g), caprylic/capric triglyceride (5 g), paraffin oil (4 g), glyceryl monostearate (2 g) and petroleum jelly (5 g) (all Sinopharm Chemical Reagent Co. Ltd) were mixed and heated to 85° C. with stirring until the mixture melted completely. Then, ammonium acryloyldimethyltaurate/VP copolymer (0.13 g), glycerin (4 g), trehalose (0.5 g; Sinopharm Chemical Reagent Co. Ltd) were mixed together with purified water (70.5 g) at 85° C. until the various components dissolved.

A third mixture was made comprising montelukast sodium (200 mg), polyethylene glycol 200 (4 g; Sinopharm Chemical Reagent Co. Ltd), phenoxyethanol (0.3 g) and ethylhexyl glycerin (0.1 g), with stirring until the montelukast dissolved.

The copolymer/water mixture was added to the sorbitan monostearate-containing mixture, followed by emulsification, stirring, and cooling to 55° C. Silicon oil (0.5 g; Sinopharm Chemical Reagent Co. Ltd) was then added, along with the montelukast-containing mixture, with mixing. Cooling to room temperature gave the finished product.

Example 11

Montelukast Ointment I

An ointment was made by first dissolving polyethylene glycol 3350 (21.3 g; Sinopharm Chemical Reagent Co. Ltd) in polyethylene glycol 400 (58.5 g; Sinopharm Chemical Reagent Co. Ltd) by heating to 60° C. with stirring. Montelukast sodium (200 mg) was dissolved in polyethylene glycol 400 (20.0 g) with stirring.

After cooling the first solution to 40-50° C., the second solution was added to it with stirring and mixing for 5 to 10 minutes. Cooling to room temperature gave the finished product.

Example 12

Montelukast Ointment II

A further ointment was made as described in Example 11 with the exception that polyethylene glycol 4000 (21.3 g, Sinopharm Chemical Reagent Co. Ltd) was dissolved in the same amount of polyethylene glycol 400 (58.5 g).

Example 13

Montelukast Aerosol Powder Spray

An aerosol powder spray based was made by adding montelukast sodium (200 mg) to ethanol (70 g; Sinopharm Chemical Reagent Co. Ltd) with stirring until it dissolved completely.

Porous starch (28 g; Sinopharm Chemical Reagent Co. Ltd) was added to the resultant solution to provide a suspension, which was subsequently filled into an aerosol spray bottle.

Example 14

Montelukast Dressing

A dressing was made by coating evenly the montelukast sodium ointment, prepared as described in Example 12 above, on a gauze (Shanghai Health Materials Factory Co., Ltd, Shanghai, China) with a flat plate and cooling to room temperature.

Example 15

Swollen Ear Model

12 Health male BALB/c mice with 6-8 weeks age and average body weight of 18-25 g supplied by Changzhou Cvens Experimental Animal Co. Ltd. were housed and cared for about 1 week prior to the experiment. The housing temperature was 25-27° C. with 74% humidity, with alternating 12 hour periods of light and darkness, and free access to food and water. The mice were randomly divided into 4 groups as described in Table 28, with 3 mice in each group.

TABLE 28

| Group | Drug concentration | Drug administration on right ear | Total amount of drugs (μg/mouse) |
|---|---|---|---|
| Model | / | xylene | / |
| Blank | / | xylene + cream without API | / |
| Dex Cream | 10 μg/μL | xylene + Dex cream | 400 |
| Mon Cream | 5 mg/g | xylene + Mon cream | 500 |

The montelukast cream (Mon Cream) is the cream described in Example 8 above. Blank cream was made following the same procedure, with our adding montelukast to the mixture. Dexamethasone cream (Dex Cream) was also made using the same procedure, replacing montelukast with dexamethasone (160 mg; Shanghai Aladdin Bio-Chem Technology Co. Ltd.).

The left ear of each mouse was used as an autologous control. The right ear of each mouse was treated with the various treatments. First 20 μL of xylene (Shanghai Aladdin Bio-Chem Technology Co., Ltd.) was applied to the right ear of each mouse, both on the inside and the outside. The ear started to swell after about 4 minutes. Then, 40 μL of the various creams were applied to the right ear of each group. The mice were put back in their cages.

The mice were sacrificed by cervical dislocation after 40 minutes. The left and right ears were cut off. A skin pouch (Electron Microscopy Sciences, Hatfield, Pa., USA) with a diameter of 8 mm was used to take a piece of the ear from the same site of both ears. The weights were recorded and the swelling rates were calculated as follows:

Swelling rate=(right ear weight−left ear weight)/left ear weight×100% and the results showed in Table 29.

TABLE 29

| Group | Weight (g) | | | | Swelling rate |
|---|---|---|---|---|---|
| | Left ear | Right ear | Difference | | |
| Model | 0.013 | 0.025 | 0.012 | 0.923 | 97.4% |
| | 0.012 | 0.021 | 0.009 | 0.750 | |
| | 0.012 | 0.027 | 0.015 | 1.250 | |
| Blank | 0.013 | 0.025 | 0.012 | 0.923 | 83.5% |
| | 0.012 | 0.023 | 0.011 | 0.917 | |
| | 0.015 | 0.025 | 0.010 | 0.667 | |
| Dex Cream | 0.013 | 0.019 | 0.006 | 0.462 | 48% |
| | 0.013 | 0.022 | 0.009 | 0.692 | |
| | 0.014 | 0.018 | 0.004 | 0.286 | |
| Mon Cream | 0.012 | 0.018 | 0.006 | 0.500 | 38.1% |
| | 0.014 | 0.020 | 0.006 | 0.429 | |
| | 0.014 | 0.017 | 0.003 | 0.214 | |

The results showed that montelukast cream significantly reduced xylene-induced swelling in mouse ears. The effect was even better than that of the well-known topical antiinflammatory medication, dexamethasone.

Example 16

Rat Scald Model I 6-8 weeks old male Sprague Dawley rats with average body weights of between 250 and 300 g were supplied by Changzhou Cvens Experimental Animal Co. Ltd. Prior to any experiments being conducted, rats were housed under standardized conditions (at a constant temperature or 22 t 2° C., with alternating 12 hour periods of light and darkness), and were fed on a standard mouse diet with water, for about a week.

A self-made mould was used. A section of bamboo was taken, and the top ⅓ along its length was removed. An oval hole was made in the bottom of the bamboo with dimensions of 2.5×4.5 cm, allowing the back of rat to be exposed to hot water. The exposed skin area was about 10-13% of its total body surface area (TBSA):

$$TBSA\ (cm^2)=K\times W\times \tfrac{2}{3},$$

where K is the correction factor (surface area to body weight/shape) constant for the given species (9.1 for the rat), and W is the body weight (in g) of the rat.

The hair on the back of the rats was shaved. 10% chloral hydrate were injected to anesthetize the rats (350 mg/kg; 3.5 mL/kg).

6 rats were divided into 2 groups of 3 rats. After anesthesia, the rats were fixed inside the mould. Adhesive tape was used to fix the limbs and the abdomen, and the bamboo was tightly attached to the back, exposing the skin through the hole. Boiling hot water at 100° C. was applied to the rats' skin for 12 seconds.

Montelukast cream (prepared as described in Example 8 above) was subsequently administered to the scald wounds in the test group, and a blank cream (the same cream with no active ingredient) was administered in the control group. Treatments were thereafter administered once a day for ten days.

Figure 11:
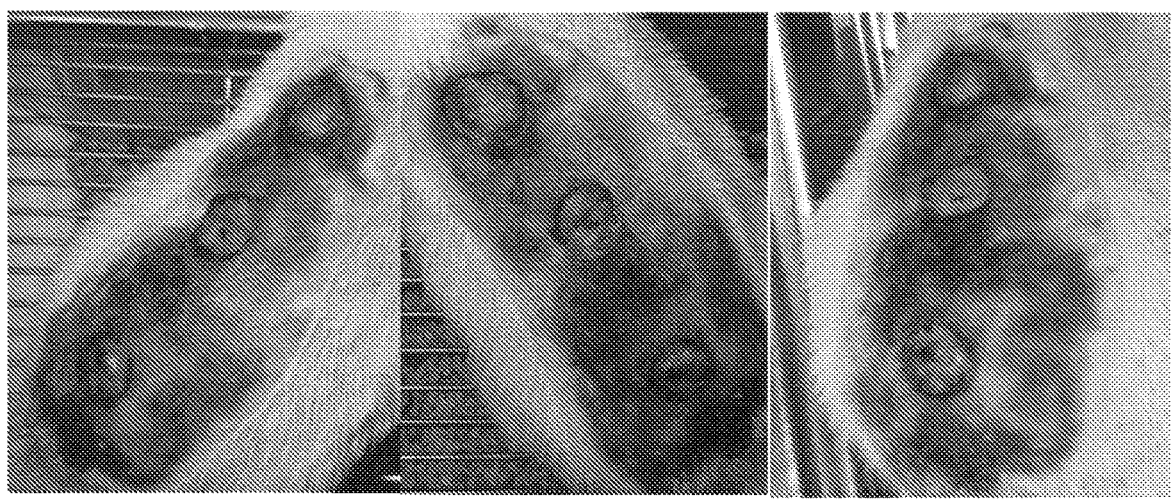
FIG. 11 shows the effect of topically-applied montelukast on scald wound healing in an in vivo rat model of Example 16.
Figure 11:

Ten days after scalding, hairs were observed to be growing in the scald area of the test group. There was no sign of hair growth in the scald area of the control group. This is shown in FIG. 11, which shows that montelukast cream helps to recover skin function after burning.

Example 17

Rat Scald Model II

8 Sprague Dawley rats were divided into two groups of 4. Scald wounds were applied in essentially the same way as that described in Example 16 above, by applying (or not applying, as appropriate) hot water at the temperature, and for the times, shown in Table 30 below.

In one of the groups, immediately after scalding, montelukast cream (only; prepared as described in Example 8 above was applied to the scald wounds. 1 g montelukast cream was used for each wound. For the other group, immediately after scalding, 0.5 mL of MAP saline solution with a concentration of 4.9 mg/mL was applied to the surface of the scald wound. After a short wait of a few minutes to allow the solvent to evaporate, a further 0.5 mL of the same MAP solution was applied, this was repeated 3 times in total. After this, 1 g of the same montelukast cream was applied on top of the MAP.

TABLE 30

| Group | Meaning | Treatment | Drug administration |
|---|---|---|---|
| Mon | Montelukast cream | Unscalded 85° C. 15 s 85° C. 10 s 75° C. 15 s | 1 g of montelukast cream applied to the surface of the scald wound |

TABLE 30-continued

| Group | Meaning | Treatment | Drug administration |
|---|---|---|---|
| MM | MAP coating, then montelukast cream | Unscalded 85° C. 15 s 85° C. 10 s 75° C. 15 s | MAP solution applied 3 times, then 1 g of montelukast cream applied to the surface of the scald wound |

Samples were taken from each rat at time zero, and then 1, 2, 3, 6 and 8 hours after scalding, using an EMS skin biopsy punch with an 8 mm diameter. The full thickness skin was removed and weighed.

Then, tissue was cut into small pieces. 9 mL of normal saline was added to 1 g of tissue, which was then ground using a Tissuelyser at 55 Hz for 60 seconds, followed by centrifuging at 8000 rpm for 10 minutes at 4° C. and the supernatant collected for HPLC analysis.

The HPLC conditions were as follows: column: Angilent ZORBAX Eclipse XDB-C8 (4.6×250 mm, 5 µm); buffers: A: 0.1% TFA (trifluoroacetic acid, (Shanghai Aladdin Bio-Chem Technology Co., Ltd.) in water, B: 0.1% TFA in acetonitrile (Merck, Darmsladt, Germany); gradient: 0-20 minutes: 49% B; flow rate: 1 mL/min; detection wavelength: 388 nm; sample volume: 20 µL.

The amount of montelukast contained in each of the samples was detected and calculated based on peak areas. A standard curve of peak area versus montelukast amount was used for the calculation.

Figure 12:
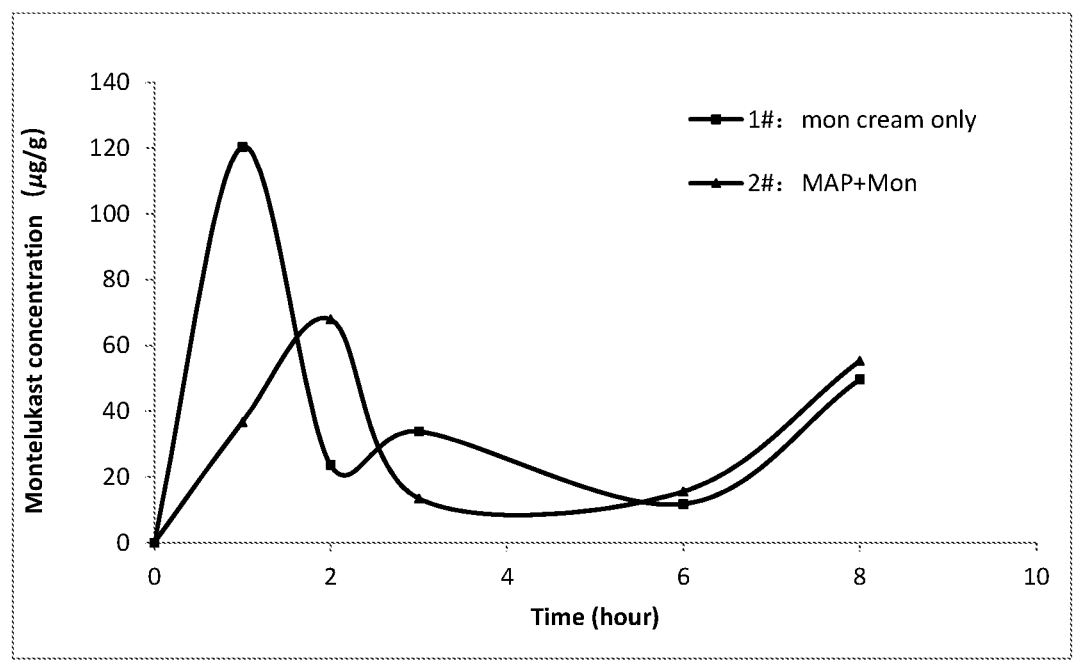
FIGS. 12 and 13 show montelukast penetration in unharmed skin and scalded skin in a similar in vivo rat model (see Example 17), in the cases of montelukast being applied topically alone (FIG. 12) and after an initial application of MAP (FIG. 13)

The results for the unscalded, intact skin samples are shown in Table 31 below and in FIG. 12.

TABLE 31

| Sampling Time (h) | Peak area | Montelukast amount (g) | Wet weight (g) | Montelukast concentrations (µg/g) |
|---|---|---|---|---|
| 0 | 756 | 0 | 0.069 | 0 |
| 1 | 171262 | 2.53 | 0.069 | 36.69 |
| 2 | 381470 | 5.44 | 0.080 | 67.98 |
| 3 | 52374 | 0.89 | 0.066 | 13.44 |
| 6 | 53490 | 0.90 | 0.058 | 15.56 |
| 8 | 244228 | 3.54 | 0.064 | 55.32 |

The results showed that on intact skin, the concentration peak was one hour later in MM group than that in Mon group. This indicated that MAP can delay the penetration of montelukast into the skin.

Figure 13:
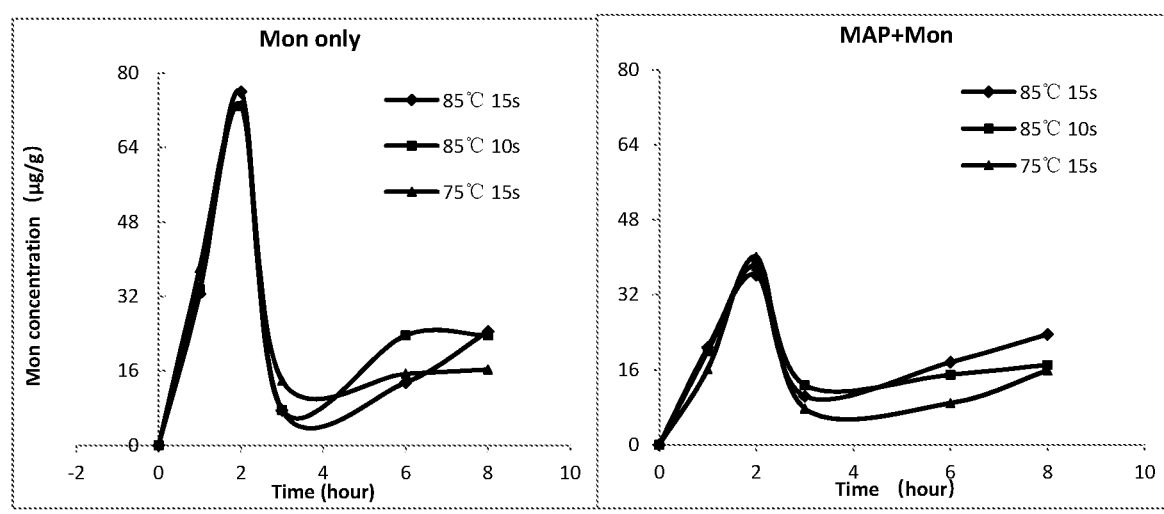

The results for scald groups were showed in FIG. 13.

Compared to intact skin, it seemed that the skin became harder to penetrate after scalding. In both Mon and MM groups, peaks of montelukast showed at 2 hours. However, the amount of montelukast contained in the samples decreased significantly over time in the MM group compared to the Mon group. These results confirm that MAP can the delay the penetration of montelukast, Irrespective of the skin conditions.

Example 18

Clinical Example of Montelukast Cream to Treat Edema in a Burns Patient

Montelukast cream was prepared according to the same method described in Example 8 above. The concentration of montelukast sodium in the cream was 5 mg/g.

Figure 14:
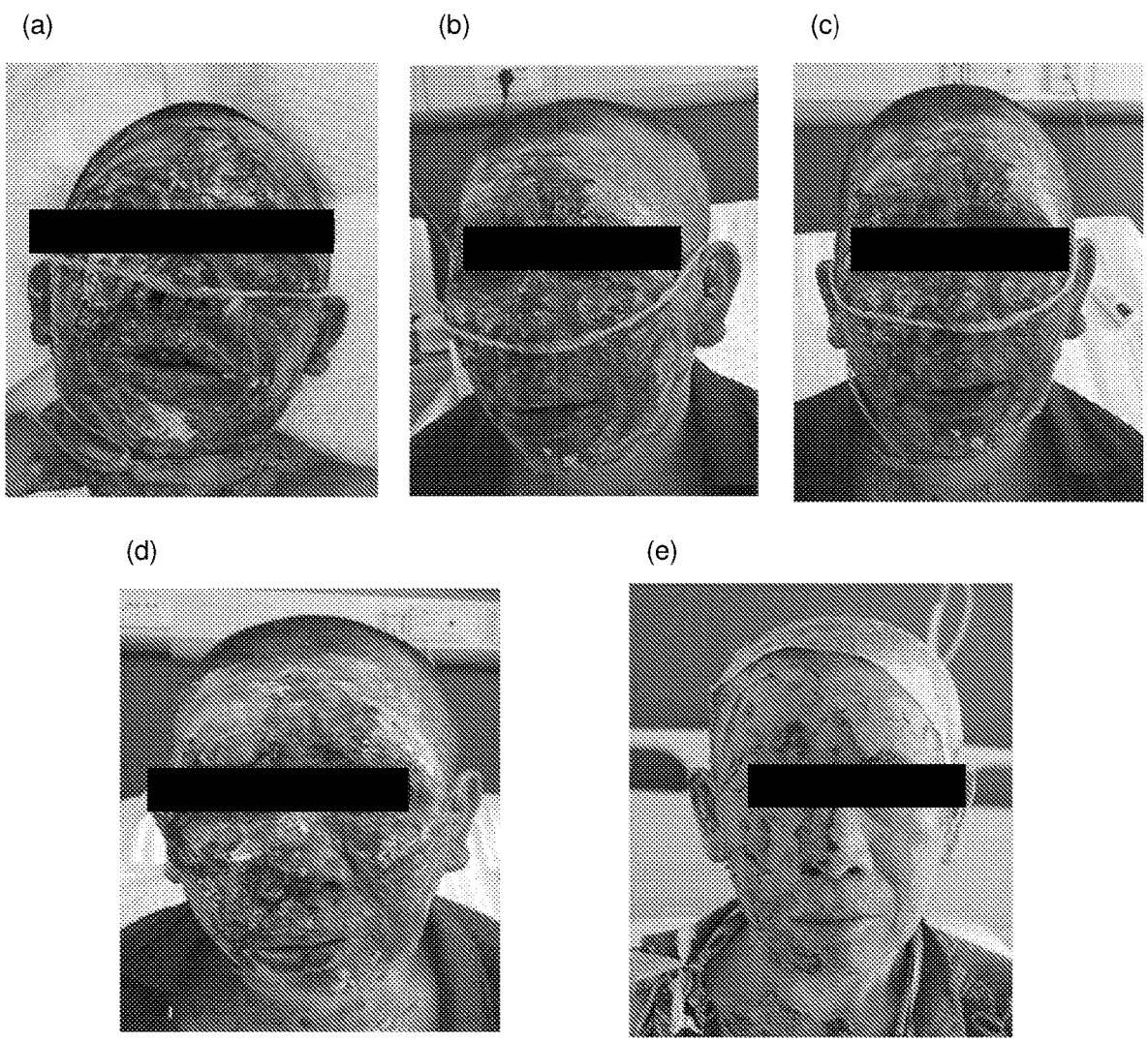
FIG. 14 shows the effect of topically applied montelukast in a patient with second degree burns compared to silver sulfadiazine treatment.

The enrolled subject in the study was a patient with second degree burns in the head and neck area (FIG. 14; photograph (a)). Montelukast cream was applied on the left side of the patient's face, starting 20 hours after the burn injuries were sustained. Silver sulfadiazine ointment, a well-recognized topical burns treatment, was applied to the right side of the face as a comparison. Both drugs were applied twice per day.

As shown in FIG. 14, one day after treatment (photograph (b)), the edema in the left side of the face was clearly being reduced faster and more extensively than on the right side. This relative improvement continued over the next few days (2 days (photograph (c)), 3 days (photograph (d)), and 14 days (photograph (e)), after treatment).

This experiment showed that montelukast cream effectively treats edema in acute inflammation stage of burns and was more effective that silver sulfazidine.

Example 19

Clinical Example of Montelukast Cream to Treat Burns Scar Itch

Montelukast cream (with a 5 mg/g concentration of montelukast sodium) was prepared according to the same method described in Example 8 above.

The enrolled subjects in the study were burn patients with old cicatricial scars. Symptoms Included Irregular shaped hypertrophic scars with pain and itching. Ambient temperature changes or emotional agitation is known to aggravate pain and/or itching.

Subjects were required to use the cream in the morning and the evening after cleansing the scar.

All of the enrolled subjects felt that itching was relieved within 8 minutes of the first use, demonstrating that montelukast cream may be used to treat burn scar itch.

Example 20

Clinical Example of Montelukast Cream to Treat Melanin Related Skin Diseases I

Montelukast cream (with a 5 mg/g concentration of montelukast sodium) was prepared according to the same method described in Example 9 above.

The enrolled subjects in the study were patients with melanin related skin diseases. Symptoms included pigmentation after burns or acne eruption. Subjects were required to use the cream in the morning and evening after facial cleansing.

All of the enrolled subjects felt that the skin colour improved after 2 weeks of use, demonstrating that montelukast cream may be used to treat melanin pigmentation and/or melanin-related skin diseases.

Example 21

Clinical Example of Montelukast Cream to Treat Melanin Related Skin Diseases II

Montelukast cream (with a 5 mg/g concentration of montelukast sodium) was prepared according to the same method described in Example 9 above.

The enrolled subject in the study was a patient with melanin related skin diseases. Symptoms included chloasma and malar rash.

A laser pre-treatment was employed to attempt to remove the worst of the symptoms. The subject was required to use the cream in the morning and evening after facial cleansing.

Figure 15:
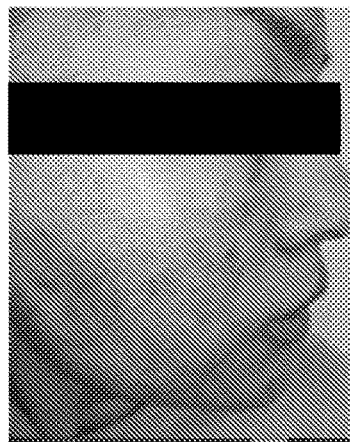
FIG. 15 shows the effect of topically applied montelukast in a patient with a melanin-related skin condition (chloasma and malar rash)
Figure 15:
Figure 15:
Figure 15:
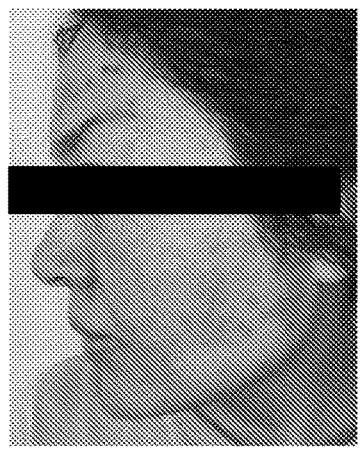
Figure 15:
Figure 15:

The subject felt that her skin colour improved after 2 weeks after 2 weeks of use. This is the case, as can be seen from FIG. 15, in which both sides of the face are seen before the laser treatment (photographs (a)), 7 days after treatment with montelukast cream commenced (photographs (b)), and 14 days after treatment with montelukast cream (photographs (c)). This demonstrates that montelukast cream may be used to treat melanin pigmentation and/or melanin-related skin diseases.

Example 22

Clinical Example of Montelukast Cream to Treat Steroid Dependent Dermatitis

Montelukast cream (with a 5 mg/g concentration of montelukast sodium) was prepared according to the same method described in Example 9 above.

The enrolled subject in the study was a patient with steroid-dependent dermatitis. Symptoms included skin redness, papules, itching and swelling.

The subject was required to use the cream in the morning and evening after facial cleansing.

Figure 16:
FIG. 16 shows the effect of topically applied montelukast in a patient with steroid-dependent dermatitis.
Figure 16:

The use of the cream was observed to relieve itching in the subject within 5 minutes. As can be seen from FIG. 16 (before (photograph (a)), and after (photograph (b)), treatment), montelukast cream may be used as an adjuvant therapy for steroid-dependent dermatitis.

The invention claimed is:

1. A method of promoting healing or recovery of a hemorrhoid-induced wound of a patient, the method comprising: topically administering a pharmaceutical formulation comprising a therapeutically effective amount of montelukast, or a pharmaceutically acceptable salt of solvate thereof, in admixture with a pharmaceutically-acceptable topical adjuvant, diluent or carrier, directly to a hemorrhoid-induced wound of a patient.

2. The method of claim 1, wherein the hemorrhoid-induced wound comprises damage to and/or below the epidermis or the dermis.

3. The method of claim 1, wherein said topically administering the pharmaceutical formulation further treats pain and/or itching associated with the hemorrhoid-induced wound or healing processes associated therewith.

4. The method of claim 1, wherein said topically administering the pharmaceutical formulation further prevents the exudation of body fluids and/or the risk of infection resulting from the hemorrhoid-induced wound, and/or further prevents physiological reactions that result from the hemorrhoid-induced wound healing processes.

5. The method of claim 1, wherein said topically administering is carried out on the skin.

6. The method of claim 1, wherein said topically administering is carried out on a mucosal surface.

7. The method of claim 1, wherein the pharmaceutical formulation is in the form of a gel, a cream or an ointment.

8. The method of claim 1, wherein the pharmaceutical formulation further comprises polyethylene glycol.

9. The method of claim 8, wherein the polyethylene glycol is polyethylene glycol 400.

10. The method of claim 1, wherein the pharmaceutical formulation further comprises at least one mussel adhesive protein or a derivative thereof.

11. The method of claim 1 further comprising:
topically administering a second pharmaceutical formulation comprising at least one mussel adhesive protein or a derivative thereof, in admixture with a pharmaceutically-acceptable adjuvant, diluent or carrier,
wherein the pharmaceutical formulation and the second pharmaceutical formulation are each suitable for administration in conjunction with the other.

12. The method of claim 11, wherein the pharmaceutical formulation and the second pharmaceutical formulation are suitable for sequential, separate and/or simultaneous administration in the treatment of the hemorrhoid-induced wound.

13. The method of claim 10, wherein the at least one mussel adhesive protein is selected from the group: mefp-1, mefp-2, mefp-3, mefp-4, mefp-5, mefp-6, and combinations thereof.

14. The method of claim 10, wherein the at least one mussel adhesive protein comprises mefp-1.

15. The method of claim 10, wherein the derivative of a mussel adhesive protein is a peptide of the sequence Ala-Lys-Pro-Ser-Tyr-Hyp-Hyp-Thr-DOPA-Lys (SEQ ID NO:1) or a salt thereof.

16. The method of claim 11, wherein the at least one mussel adhesive protein is selected from the group: mefp-1, mefp-2, mefp-3, mefp-4, mefp-5, mefp-6, and combinations thereof.

17. The method of claim 11, wherein the at least one mussel adhesive protein comprises mefp-1.

18. The method of claim 11, wherein the derivative of a mussel adhesive protein is a peptide of the sequence Ala-Lys-Pro-Ser-Tyr-Hyp-Hyp-Thr-DOPA-Lys (SEQ ID NO:1) or a salt thereof.

19. A method of promoting healing or recovery of a hemorrhoid-induced wound of a patient, the method comprising: providing a pharmaceutical formulation that is in the form of a gel, a cream or an ointment and comprises a therapeutically effective amount of montelukast, or a pharmaceutically acceptable salt of solvate thereof, in admixture with a pharmaceutically-acceptable topical adjuvant, diluent or carrier; topically applying the pharmaceutical formulation directly to a hemorrhoid-induced wound of a patient, wherein the hemorrhoid-induced wound comprises injury to the skin or mucosa, damage to and/or below the epidermis or the dermis, or damage to a subcutaneous tissue, a submucosal tissue or an internal organ, and wherein said topically applying promotes healing or recovery of the hemorrhoid-induced wound.

\* \* \* \* \*